US008324364B2

(12) United States Patent
Whiteford et al.

(10) Patent No.: US 8,324,364 B2
(45) Date of Patent: Dec. 4, 2012

(54) COMPOSITIONS AND METHODS FOR THE IDENTIFICATION OF A CARBAPENEMASE GENE

(75) Inventors: Craig C. Whiteford, York, PA (US); Charles Yu, Lutherville, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/108,365

(22) Filed: May 16, 2011

(65) Prior Publication Data

US 2012/0071642 A1 Mar. 22, 2012

Related U.S. Application Data

(62) Division of application No. 12/098,823, filed on Apr. 7, 2008, now Pat. No. 7,968,292.

(60) Provisional application No. 60/910,535, filed on Apr. 6, 2007.

(51) Int. Cl.
*C07H 21/04* (2006.01)
(52) U.S. Cl. ..................................... 536/24.33
(58) Field of Classification Search ........................ None
See application file for complete search history.

(56) References Cited

U.S. PATENT DOCUMENTS

| | | | | |
|---|---|---|---|---|
| 2001/0053519 | A1* | 12/2001 | Fodor et al. ....................... | 435/6 |
| 2004/0002080 | A1 | 1/2004 | Hanson | |
| 2005/0260633 | A1 | 11/2005 | Hanson et al. | |

OTHER PUBLICATIONS

Moland et al. (J Antimicrob Chemother. Mar. 2003;51(3):711-4).*
GenBank Accession No. AY034847 (Mar. 13, 2003).*
Buck et al (Biotechniques. 1999. 27(3): pp. 528-536).*
Yigit et al. (Antimicrob Agents Chemother. Apr. 2001;45(4):1151-61).
GenBank Accession No. AF297554 (Mar. 26, 2001).
Buck et al ("Design Strategies and Performance of Custom DNA Sequencing Primers" Biotechniques. 1999. 27(3): pp. 528-536).
Lowe et al. (Nucleic Acids Research, vol. 18, No. 7, p. 1757-1761, 1990).
Stratagene ("Gene Characterization Kits" 1988).
Bratu, S., et al., "Carbapenemase-Producing *Klebsiella pneumoniae* in Brooklyn, NY: Molecular Epidemiology and in vitro Activity of Polymyxin B and Other Agents," Journal of Antimicrobial Chemotherapy, 2005, pp. 128-132, vol. 56.
Bratu, S., et al., "Rapid Spread of Carbapenem-Resistant *Klebsiella pneumoniae* in New York City," Arch. Intern. Med., 2005, pp. 1430-1435, vol. 165.
Livermore, D., and N. Woodford, "Carbapenemases: A Problem in Waiting?," Current Opinion in Microbiology, 2000, pp. 489-495, vol. 3(5).
Moland, E., et al., "Plasmid-Mediated, Carbapenem-Hydrolysing .beta.-Lactamase, KPC-2, in *Klebsiella pneumoniae* Isolates," Journal of Antimicrobial Chemotherapy, 2003, pp. 711-714, vol. 51.

Naas, T., et al., "Plasmid-Mediated Carbapenem-Hydrolysing .beta.-Lactamase KPC in a *Klebsiella pneumoniae* Isolate from France," Antimicrobial Agents and Chemotherapy, 2005, pp. 4423-4424, vol. 49(10).
Paterson, D. L., "Recommendation for Treatment of Severe Infections Caused by Enterobacteriaceae Producing Extended-Spectrum .beta.-Lactamases (ESBLs)," Clinical Microbiology and Infection, 2000, pp. 460-463, vol. 6(9).
Woodford, N., et al., "Outbreak of *Klebsiella pneumoniae* Producing a New Carbapenem-Hydrolyzing Class A .beta.-Lactamase, KPC-3, in a New York Medical Center," Antimicrobial Agents and Chemotherapy, 2004, pp. 4793-4799, vol. 48(12).
Yigit, H., et al., "Novel Carbapenem-Hydrolyzing .beta.-Lactamase, KPC-1, from a Carbapenem-Resistant Strain of *Klebsiella pneumoniae*," Antimicrobial Agents and Chemotherapy, 2001, pp. 1151-1161, vol. 45(4).
Yigit, H., et al "Carbapenem-Resistant Strain of *Klebsiella oxytoca* Harboring Carbapenem-Hydrolyzing .beta.-Lactamase KPC-2," Antimicrobial Agents and Chemotherapy, 2003, pp. 3881-3889, vol. 47(12).
GenBank Report for Accession No. AF297554, Direct Submission on Aug. 19, 2000.
GenBank Report for Accession No. AY034847, Direct Submission on May 15, 2001.
GenBank Report for Accession No. AY494718, Direct Submission on Dec. 3, 2003.
GenBank Report for Accession No. DQ523564, Direct Submission on May 2, 2006.
GenBank Report for Accession No. DQ897687, Direct Submission on Aug. 10, 2006.
Bratu, S., et al., "Detection and Spread of *Escherichia coli* Possessing the Plasmid-Borne Carbapenemase KPC-2 in Brooklyn, New York," Clinical Infectious Diseases, 2007, pp. 972-975, vol. 44 (7).
Deshpande, L., et al., "Occurrence and Characterization of Carbapenemase-Producing Enterobacteriaceae: Report from the SENTRY Antimicrobial Surveillance Program (2000-2004)," Microbial Drug Resistance, 2006, pp. 223-230, vol. 12 (4). Iwaya, A., et al., "Rapid and Quantitative Detection of Blood *Serratia marcescens* by a Real-Time PCR Assay: Its Clinical Application and Evaluation in a Mouse Infection Model," FEMS Microbiology Letters, 2005, pp. 163-170, vol. 248 (2).
Lee, H., et al., "Prevalence of Decreases Susceptibility to Carbapenems Among *Serratia marcescens*, Enterbacter cloacae, and *Citrobacter freundii* and Investigation of Carbapenemases," Diagnostic Microbiology and Infectious Disease, 2005, pp. 331-336,vol. 52(4).

* cited by examiner

*Primary Examiner* — Christopher M. Babic
(74) *Attorney, Agent, or Firm* — Lerner, David, Littenberg, Krumholz & Mentlik, LLP

(57) ABSTRACT

Compositions and methods for the rapid and sensitive detection of a carbapenemase in a sample are provided. The compositions include novel primer and probe compositions for use in detecting the presence of this enzyme in a sample, particularly using PCR methods. These primers and probe sets can be used in amplification methods (such as PCR, particularly quantitative PCR) and packaged into kits for use in amplification methods for the purpose of detecting carbapenemase in a test sample, particularly a patient sample, particularly a direct sample. Thus, in one embodiment, the present invention provides for novel oligonucleotide primers set forth in SEQ ID NOs: 1, 2, 4, 5, 7, 8, 14, 15, 17, 18, and 20, and the novel oligonucleotide probe sequences set forth in SEQ ID NOs: 3, 6, 9, 16, and 19. These sequences can be used in a method of detecting carbapenemase in a sample.

5 Claims, 2 Drawing Sheets

SEQUENCE LISTING

```
<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 1
cgcggaacca ttcgctaa                                                 18

<210> SEQ ID NO 2
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 2
cggtatccat cgcgtacaca                                               20

<210> SEQ ID NO 3
<211> LENGTH: 24
<212> TYPE: DNA
<213> ORGANISM: Artificial Sequence
<220> FEATURE:
<223> OTHER INFORMATION: oligonucleotide probe

<400> SEQUENCE: 3
ctcgaacagg actttggcgg ctcc                                          24

<210> SEQ ID NO 4
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 4
ggcaaaaatg cgctggtt                                                 18

<210> SEQ ID NO 5
<211> LENGTH: 18
<212> TYPE: DNA
<213> ORGANISM: Artificial sequence
```

```
<220> FEATURE:
<223> OTHER INFORMATION: oligonucleotide primer

<400> SEQUENCE: 5
gccaccgtca tgcctgtt                                                 18

<210> SEQ ID NO 6
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 6
cgtggtcacc catctcggaa aaatatctga                                    30

<210> SEQ ID NO 7
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 7
ggcgcgcacc tattgtgt                                                 18

<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 8
cgctgtgctt gtcatccttg t                                             21

<210> SEQ ID NO 9
<211> LENGTH: 20
<212> TYPE: DNA
<213> ORGANISM: Artificial Sequence
<220> FEATURE:
<223> OTHER INFORMATION: oligonucleotide probe

<400> SEQUENCE: 9
ccgtctacac ccgggcgcct                                               20

<210> SEQ ID NO 10
<211> LENGTH: 1377
<212> TYPE: DNA
<213> ORGANISM: Klebsiella pneumoniae
<220> FEATURE:
<221> NAME/KEY: misc_feature
<222> LOCATION: (0)...(0)
<223> OTHER INFORMATION: KPC-1 isoform (GenBank Acc No. AF297554)

<400> SEQUENCE: 10
cggggcagtt acagccgtta cagcctctgg agagggagcg gcttgccgct cggtgataat    60
cccagctgta gcggcctgat tacatccggc cgctacacct agctccacct tcaaacaagg   120
aatatcgttg atgtcactgt atcgccgtct agttctgctg tcttgtctct catggccgct   180
ggctggcttt tctgccaccg cgctgaccaa cctcgtcgcg gaaccattcg ctaaactcga   240
acaggacttt ggcggctcca tcggtgtgta cgcgatggat accggctcag gcgcaactgt   300
aagttaccgc gctgaggagc gcttcccact gtgcagctca ttcaagggct tcttgctgc   360 cgctgtgctg gctcgcagcc agcagcaggc cggcttgctg gacacaccca tccgttacgg   420
```

```
caaaaatgcg ctggttccgt ggtcacccat ctcggaaaaa tatctgacaa caggcatgac    480
ggtggcggag ctgtccgcgg ccgccgtgca atacagtgat aacgccgccg ccaatttgtt    540
gctgaaggag ttgggcggcc cggccgggct gacggccttc atgcgctcta tcggcgatac    600
cacgttccgt ctggaccgct gggagctgga gctgaactcc gccatcccaa gcgatgcgcg    660
cgatacctca tcgccgcgcg ccgtgacgga aagcttacaa aaactgacac tgggctctgc    720
actggctgcg ccgcagcggc agcagtttgt tgattggcta aagggaaaca cgaccggcaa    780
ccaccgcatc cgcgcggcgg tgccggcaga ctgggcagtc ggagacaaaa ccggaacctg    840
cggagtgtat ggcacggcaa atgactatgc cgtcgtctgg cccactgggc gcgcacctat    900
tgtgttggcc gtctacaccc gggcgcctaa caaggatgac aagcacagcg aggccgtcat    960
cgccgctgcg gctagactcg cgctcgaggg attgggcgtc aacgggcagt aaggctctga   1020
aaatcatcta ttggcccacc accgccgccc ttgcgggcgg catggattac caaccactgt   1080
cacatttagg ctaggagtct gcgcggcaga gccgtgtgac cggttttctg tagagcactg   1140
acgatggcgg cggcgctctc tgcaattggc aaggcgtcgg cgccaaggat accaatcttg   1200 cggcgcgcg cgtgttatga cgactggggt gcatttgagc cgccccattt aaccttcgcc   1260
ctcacagata cgccattcgc ctcaaattta gcgccatgca gacgagcttc cactcggctt   1320
gcaccttgtc caggcccctc atgctgaact gacgcaatcc catcaccgcc ttgatca     1377

<210> SEQ ID NO 11
<211> LENGTH: 960
<212> TYPE: DNA
<213> ORGANISM: Klebsiella pneumoniae
<220> FEATURE:
<221> NAME/KEY: misc_feature
<222> LOCATION: (0)...(0)
<223> OTHER INFORMATION: KPC-3 isoform (Genbank Acc No. AF395881)

<400> SEQUENCE: 11
atgtcactgt atcgccgtct agttctgctg tcttgtctct catggccgct ggctggcttt     60
tctgccaccg cgctgaccaa cctcgtcgcg gaaccattcg ctaaactcga acaggacttt    120
ggcggctcca tcggtgtgta cgcgatggat accggctcag gcgcaactgt aagttaccgc    180
gctgaggagc gcttcccact gtgcagctca ttcaagggct tcttgctgcc gctgtgctg    240 gctcgcagcc agcagcaggc cggcttgctg gacacaccca tccgttacgg caaaaatgcg    300
ctggttccgt ggtcacccat ctcggaaaaa tatctgacaa caggcatgac ggtggcggag    360
ctgtccgcgg ccgccgtgca atacagtgat aacgccgccg ccaatttgtt gctgaaggag    420
ttgggcggcc cggccgggct gacggccttc atgcgctcta tcggcgatac cacgttccgt    480
ctggaccgct gggagctgga gctgaactcc gccatcccag gcgatgcgcg cgatacctca    540
tcgccgcgcg ccgtgacgga aagcttacaa aaactgacac tgggctctgc actggctgcg    600
ccgcagcggc agcagtttgt tgattggcta aagggaaaca cgaccggcaa ccaccgcatc    660
cgcgcggcgg tgccggcaga ctgggcagtc ggagacaaaa ccggaacctg cggagtgtat    720
ggcacggcaa atgactatgc cgtcgtctgg cccactgggc gcgcacctat tgtgttggcc    780
gtctacaccc gggcgcctaa caaggatgac aagtacagcg aggccgtcat cgccgctgcg    840
gctagactcg cgctcgaggg attgggcgtc aacgggcagt aaggctctga aaatcatcta    900
ttggcccacc accgccgccc ttgcgggcgg catggattac caaccactgt cacatttagg    960

<210> SEQ ID NO 12
<211> LENGTH: 918
```

```
<212> TYPE: DNA
<213> ORGANISM: Klebsiella pneumoniae
<220> FEATURE:
<221> NAME/KEY: misc_feature
<222> LOCATION: (0)...(0)
<223> OTHER INFORMATION: KPC-2 isoform (Genbank Acc No. AY034847)

<400> SEQUENCE: 12
cgttgatgtc actgtatcgc cgtctagttc tgctgtcttg tctctcatgg ccgctggctg      60
gcttttctgc caccgcgctg accaacctcg tcgcggaacc attcgctaaa ctcgaacagg     120
actttggcgg ctccatcggt gtgtacgcga tggataccgg ctcaggcgca actgtaagtt     180
accgcgctga ggagcgcttc ccactgtgca gctcattcaa gggctttctt gctgccgctg     240
tgctggctcg cagccagcag caggccggct tgctggacac acccatccgt tacggcaaaa     300
atgcgctggt tccgtggtca cccatctcgg aaaaatatct gacaacaggc atgacggtgg     360
cggagctgtc cgcggccgcc gtgcaataca gtgataacgc cgccgccaat ttgttgctga     420
aggagttggg cggcccggcc gggctgacgg ccttcatgcg ctctatcggc gataccacgt     480
tccgtctgga ccgctgggag ctggagctga actccgccat cccaggcgat gcgcgcgata     540
cctcatcgcc gcgcgccgtg acggaaagct acaaaaact gacactgggc ctgcactgg      600 ctgcgccgca gcggcagcag tttgttgatt ggctaaaggg aaacacgacc ggcaaccacc     660
gcatccgcgc ggcggtgccg gcagactggg cagtcggaga caaaaccgga acctgcggag     720
tgtatggcac ggcaaatgac tatgccgtcg tctggcccac tgggcgcgca cctattgtgt     780
tggccgtcta cacccgggcg cctaacaagg atgacaagca cagcgaggcc gtcatcgccg     840
ctgcggctag actcgcgctc gagggattgg gcgtcaacgg cagtaaggc tctgaaaatc      900 atctattggc ccaccacc                                                  918

<210> SEQ ID NO 13
<211> LENGTH: 881
<212> TYPE: DNA
<213> ORGANISM: Klebsiella pneumoniae
<220> FEATURE:
<221> NAME/KEY: misc_feature
<222> LOCATION: (0)...(0)
<223> OTHER INFORMATION: KPC-4 isoform (Genbank Acc No. AY700571)

<400> SEQUENCE: 13
tgtcactgta tcgccgtcta gttctgctgt cttgtctctc atggccgctg gctggctttt      60
ctgccaccgc gctgaccaac ctcgtcgcgg aaccattcgc taaactcgaa caggactttg     120
gcggctccat cggtgtgtac gcgatggata ccggctcagg cgcaactgta agttaccgcg     180
ctgaggagcg cttcccactg tgcagctcat tcaagggctt tcttgctgcc gctgtgctgg     240
ctcgcagcca gcagcaggcc ggcttgctgg acacacccat ccgttacggc aaaaatgcgc     300
tggttcggtg gtcacccatc tcggaaaaat atctgacaac aggcatgacg gtggcggagc     360
tgtccgcggc cgccgtgcaa tacagtgata acgccgccgc caatttgttg ctgaaggagt     420
tgggcggccc ggccgggctg acggccttca tgcgctctat cggcgatacc acgttccgtc     480
tggaccgctg ggagctggag ctgaactccg ccatcccagg cgatgcgcgc gataccctcat     540 cgccgcgcgc cgtgacggaa agcttacaaa aactgacact gggctctgca ctggctgcgc     600
cgcagcggca gcagtttgtt gattggctaa agggaaacac gaccggcaac caccgcatcc     660
gcgcggcggt gccggcagac tgggcagtcg agacaaaaac cggaacctgc ggagggtatg     720
gcacggcaaa tgactatgcc gtcgtctggc ccactgggcg cgcacctatt gtgttggccg     780
tctacacccg ggcgcctaac aaggatgaca agcacagcga ggccgtcatc gccgctgcgg     840
```

-continued ctagactcgc gctcgaggga ttgggcgtca acgggcagta a            881

<210> SEQ ID NO 14
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 14
gaaccattcg ctaaactcga aca            23

<210> SEQ ID NO 15
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 15
ccgtcatgcc tgttgtcaga            20

<210> SEQ ID NO 16
<211> LENGTH: 15
<212> TYPE: DNA
<213> ORGANISM: Artificial Sequence
<220> FEATURE:
<223> OTHER INFORMATION: oligonucleotide probe

<400> SEQUENCE: 16
cccatctcgg aaaaa            15

<210> SEQ ID NO 17
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 17
cgccgtgcaa tacagtgata ac            22

<210> SEQ ID NO 18
<211> LENGTH: 14
<212> TYPE: DNA
<213> ORGANISM: Artificial Sequence
<220> FEATURE:
<223> OTHER INFORMATION: oligonucleotide primer

<400> SEQUENCE: 18
cgggccgccc aact            14

<210> SEQ ID NO 19
<211> LENGTH: 18
<212> TYPE: DNA
<213> ORGANISM: Artificial Sequence
<220> FEATURE:
<223> OTHER INFORMATION: oligonucleotide probe

<400> SEQUENCE: 19
ccgccaattt gttgctga            18

<210> SEQ ID NO 20
<211> LENGTH: 16
<212> TYPE: DNA
<213> ORGANISM: Artificial Sequence

```
<220> FEATURE:
<223> OTHER INFORMATION: oligonucleotide primer

<400> SEQUENCE: 20
actgggcgcg caccta                                                      16
```

COMPOSITIONS AND METHODS FOR THE IDENTIFICATION OF A CARBAPENEMASE GENE

CROSS-REFERENCE TO RELATED APPLICATIONS

This application is a divisional of U.S. application Ser. No. 12/098,823, filed on Apr. 7, 2008, now U.S. Pat. No. 7,968,292, which claims the benefit of U.S. Provisional Application No. 60/910,535, filed Apr. 6, 2007, the disclosures of which are incorporated herein by reference.

REFERENCE TO SEQUENCE LISTING SUBMITTED ELECTRONICALLY

The official copy of the sequence listing was submitted electronically via EFS-Web as an ASCII formatted sequence listing with a file named 341605SEQLIST.txt, created on Apr. 4, 2008, and having a size of 8.62 kilobytes and is filed concurrently with the specification. The sequence listing contained in this ASCII formatted document is part of the specification and is herein incorporated by reference in its entirety.

FIELD OF THE INVENTION

The invention relates to compositions and methods for the rapid identification of the carbapenemase gene of *Klebsiella* that confers antibiotic resistance.

BACKGROUND OF THE INVENTION

The Enterobacteriaceae are a large family of bacteria, including many of the more familiar pathogens, such as *Salmonella* and *Escherichia coli*. Members of genera belonging to the Enterobacteriaceae family have earned a reputation placing them among the most pathogenic and most often encountered organisms in clinical microbiology. These large gram-negative rods are usually associated with intestinal infections but can be found in almost all natural habitats. Many members of this family are a normal part of the gut flora found in the intestines of humans and other animals, while others are found in water or soil, or are parasites on a variety of different animals and plants. *Escherichia coli*, better known as *E. coli*, is one of the most important model organisms, and its genetics and biochemistry have been closely studied.

*Klebsiella pneumoniae* is a gram-negative, nonmotile, encapsulated, lactose-fermenting, facultatively anaerobic bacterium found in the normal flora of the mouth, skin, and intestines. It is clinically the most important member of the *Klebsiella* genus of Enterobacteriaceae. *K. pneumoniae* can cause bacterial pneumonia, though it is more commonly implicated in hospital-acquired urinary tract and wound infections, particularly in immunocompromised individuals. *Klebsiella* ranks second to *E. coli* for urinary tract infections in older persons. It is also an opportunistic pathogen for patients with chronic pulmonary disease, enteric pathogenicity, nasal mucosa atrophy, and rhinoscleroma. Feces are the most significant source of patient infection, followed by contact with contaminated instruments. *K. pneumoniae* is an increasingly nosocomial infection as antibiotic resistant strains continue to appear.

*Klebsiella* possesses a chromosomal class A beta-lactamase giving it inherent resistance to ampicillin. Many strains have acquired an extended-spectrum beta-lactamase (ESBL) with additional resistance to carbenicillin, ampicillin, quinolones, and increasingly to ceftazidime. Carbapenem antibiotics have been important agents for the management of gram-negative infections, particularly when caused by difficult nosocomial pathogens.

Carbapenems have the broadest activity spectra of any beta-lactam antibiotic and are often the most appropriate agents for use in the treatment of infections caused by multi-resistant gram-negative bacteria. Carbapenems are considered to be the agents of choice for the treatment of infections due to Enterobacteriaceae possessing extended-spectrum beta-lactamases (ESBLs). The prevalence of ESBL-producing *Klebsiella pneumoniae* has been rising in the United States, and is approaching 50% of isolates in some regions. When such high rates of ESBL-producing organisms are encountered, carbapenems become an increasingly important therapeutic option. Over the past few years, a progressive increase in carbapenem-resistant gram-negative bacteria has been observed in some areas. In the United States, carbapenem resistance has been largely attributed to expression of a class C cephalosporinase and loss of outer membrane porins in isolates of *Acinetobacter baumannii*, *Pseudomonas aeruginosa*, and rarely, *K. pneumoniae*. Carbapenem-hydrolysing beta-lactamases (carbapenemases) have been rarely recovered in *K. pneumoniae*. However, isolates possessing carbapenemases KPC-1, KPC-2, and KPC-3 have been recently identified in the northeastern United States. These isolates are often resistant to multiple antibiotic classes, presenting clinicians with very limited therapeutic options.

The emergence of highly resistant organisms causing outbreaks of infections is a significant problem that the microbiology and infectious disease community have been dealing with for several years. Now, the emergence of carbapenem-resistant *Klebsiella pneumoniae* can be added to the growing list of highly resistant organisms. An outbreak of carbapenem-resistant *K. pneumoniae* infections that occurred in multiple hospitals in New York City in 2005 brought widespread attention to these organisms.

KPC enzymes are beta-lactamases that mediate resistance to extended-spectrum cephalosporins as well as resistance to the carbapenems. These carbapenemases were first reported in 2001 in North Carolina but have now been isolated in various parts of the United States, most frequently on the East coast. Detection of isolates that produce a carbapenemase is important for better management of therapy and for infection control.

SUMMARY OF THE INVENTION

Compositions and methods for the rapid and sensitive detection of a carbapenemase gene that confers antibiotic resistance are provided. The compositions comprise oligonucleotide novel primer and probe sets for use in detecting the presence of this gene in a sample. These primers and probe sets can be used in amplification methods (such as PCR, particularly quantitative PCR) and packaged into kits for use in amplification methods for the purpose of detecting the presence of a carbapenemase gene in a test sample, particularly a patient sample, whereby detection of the gene is indicative that the sample comprises a bacterium that is resistant to carbapenems.

Thus, in one embodiment, the present invention provides for novel oligonucleotide primers set forth in SEQ ID NOs:1, 2, 4, 5, 7, 8, 14, 15, 17, 18, and 20 and the novel oligonucleotide probe sequences set forth in SEQ ID NOs:3, 6, 9, 16, and 19. These sequences can be used in a method of detecting a carbapenemase gene in a sample, the presence of which is indicative that the sample comprises a bacterium having carbapenem resistance.

Further provided are kits useful for the detection of a carbapenemase gene in a sample, where the kits comprise a composition according to the present invention. The kits may further comprise instructions for using the provided composition in a polymerase-based amplification reaction, for example, PCR or QPCR.

In another embodiment, the present invention relates to a method of detecting a carbapenemase in a sample using polymerase-based amplification of a target nucleic acid region present in the bacteria, the method comprising: (a) providing a test sample suspected of containing an enterobacterium having carbapenem resistance, (b) contacting the sample with a composition of the invention under conditions sufficient to provide polymerase-based nucleic acid amplification products comprising a target nucleic acid region of a nucleotide sequence encoding a carbapenemase; and (c) detecting the presence of the nucleic acid amplification products as an indication of the presence of a carbapenemase in the test sample. In various embodiments, the test sample is a direct sample, and the methods and compositions of the invention are capable of detecting the presence of carbapenemase in the direct sample at a concentration of bacteria that is within the range of bacterial load typically found in a sample collected from a subject infected with that bacterium.

The present invention also relates to use of the primers according to the present invention, wherein the primers or probes have the sequences according to any of the sequences as defined in SEQ ID NOS:1-9 and 14-20 and 14-20.

DETAILED DESCRIPTION OF THE INVENTION

I. Overview

Figure 1:
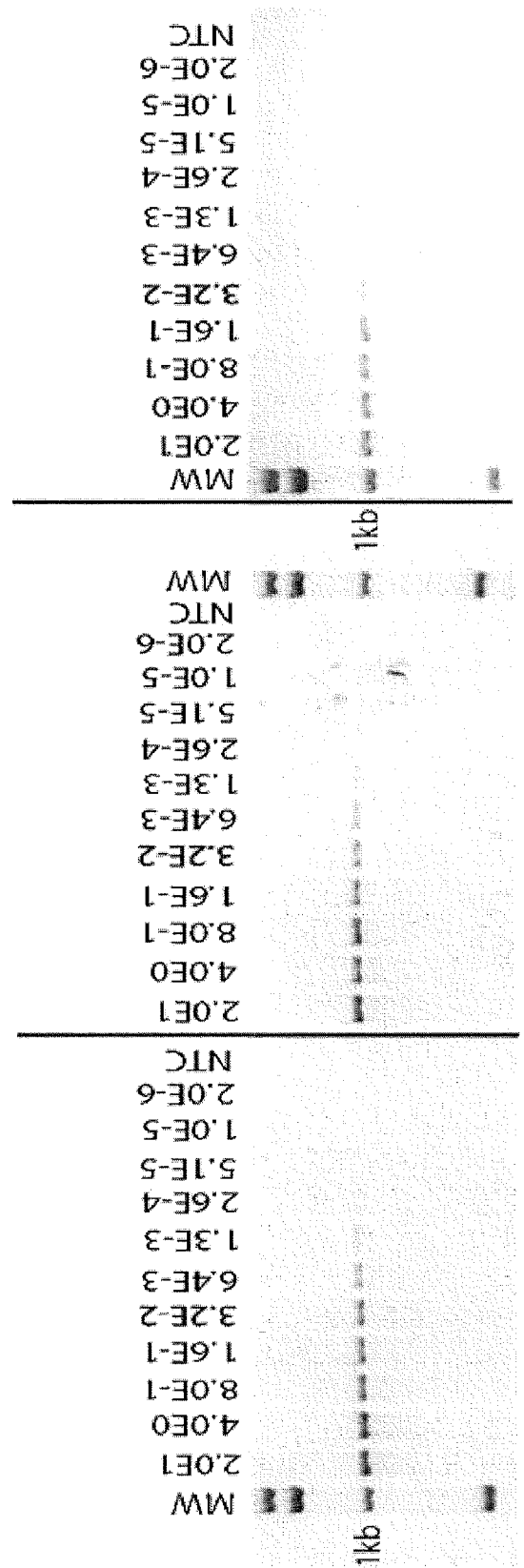
FIG. 1: Sensitivity experiments for Standard PCR. The same DNA dilution scheme (20 ng to 2 fg) was also used for the standard PCR primers. The reliable positive call was based on the ability to reliably detect a band within all the three replicates. Using this criteria, a reliable positive for the standard PCR primers is 32 pg, and thus the sensitivity is 32 pg (1,000 genomic equivalents).

Provided herein are novel methods and compositions for detecting the presence of carbapenemase in a sample suspected of having a bacterium that produces carbapenemase. Screening isolates for carbapenemase production is difficult when using routine susceptibility testing methods, due to the sometimes low-level of enzyme expression or poor discrimination from other resistance mechanisms (such as impermeability or target modification). Some phenotypic methods for detection/identification of carbapenemases have been described in the literature, but they are typically not standardized, and some are not feasible for routine clinical lab testing due to the level of expertise and/or specialized equipment needed. Scientific committees (e.g., CLSI) currently make no recommendations regarding methods for carbapenemase detection. Accordingly, there is a need for a rapid reliable test for screening for bacteria containing carbapenemases.

The methods and compositions of the present invention are directed to the detection and/or quantification of a plasmid-borne beta-lactamase gene, more particularly, the carbapenemase antibiotic resistance gene, and allow for the rapid identification of this antibiotic resistance gene. Detection of this gene in a test sample is indicative that the sample comprises a bacterium that produces carbapenemase. The method involves the use of a polymerase-based amplification method, particularly polymerase chain reaction. As used herein, "polymerase chain reaction" or "PCR" refers to an in vitro method for amplifying a specific polynucleotide template sequence (or "target nucleic acid").

Carbapenemases represent an important emerging resistance mechanism among Enterobacteriaceae. Accordingly, the methods of the invention are useful for detecting carbapenem resistance in members of the Enterobacteriaceae, including, but not limited to, *Pseudomonas aeruginosa, Acinetobacter baumannii, Klebsiella pneumoniae, Klebsiella oxytoca, Enterobacter sp., Salmonella enterica, E. coli*, and the like. Carbapenemases confer resistance to the carbapenem class of antibiotics that includes imipenem, meropenem, and ertapenem.

The compositions and methods of the invention provide a rapid and efficient test for the detection of a gene encoding carbapenemase or carbapenem-hydrolysing beta-lactamase, and thus the presence of carbapenemase in a sample. The detection of carbapenemase has represented a problem for clinical laboratories because carbapenemase is associated with positive extended-spectrum beta-lactamase (ESBL) confirmation tests (clavulanate-potentiated activities of ceftriaxone, ceftazidime, cefepime, and aztreonam). Thus, a failure to recognize the significance of reduced carbapenem susceptibility in the isolates that are susceptible to imipenem or meropenem may result in the isolates being incorrectly identified as ESBL producers.

II. Compositions

Nucleotide Sequences

The nucleotide sequences for carbapenemase from several isolates of *Klebsiella pneumoniae* are provided in SEQ ID NOs: 10-13. The primer and probe sequences of the invention are also provided as SEQ ID NOs: 1-9 and 14-20. The primer and probe sets include the forward primer set forth in SEQ ID NO:1, reverse primer set forth in SEQ ID NO:2, and nucleic acid probe set forth in SEQ ID NO:3; the forward primer set forth in SEQ ID NO:4, reverse primer set forth in SEQ ID NO:5, and nucleic acid probe set forth in SEQ ID NO:6; the forward primer set forth in SEQ ID NO:7, reverse primer set forth in SEQ ID NO:8, and nucleic acid probe set forth in SEQ ID NO:9, the forward primer set forth in SEQ ID NO:14, reverse primer set forth in SEQ ID NO:2, and nucleic acid probe set forth in SEQ ID NO:3, the forward primer set forth in SEQ ID NO:4, reverse primer set forth in SEQ ID NO:15, and nucleic acid probe set forth in SEQ ID NO:16, the forward primer set forth in SEQ ID NO:20, reverse primer set forth in SEQ ID NO:8, and nucleic acid probe set forth in SEQ ID NO:9, and the forward primer set forth in SEQ ID NO:17, reverse primer set forth in SEQ ID NO:18, and nucleic acid probe set forth in SEQ ID NO:19. These primer and probe sets can be used in a polymerase-based amplification method, for example, a real-time PCR method, for the rapid identification of the carbapenemase antibiotic resistance gene. The primer and probe sets are universal in that they can recognize all of the known isoforms of the *Klebsiella pneumoniae* carbapenemase (KPC) gene as well as detect carbapenemase genes in other enterobacteria. While particular primer and probe sequences have been identified, it is recognized that the sequences may vary by the addition or substitution of nucleotides.

Sample Source

Representative biological samples that can be used in practicing the methods of the invention include nasal swabs, throat swabs, feces, dermal swabs, blood (including blood culture), sputum, bronchio-alveolar lavage, bronchial aspirates, lung tissue, and urine. Collection and storage methods of biological samples are known to those of skill in the art. Biological samples can be processed by plating and growing the bacteria. In a preferred embodiment, the samples are direct samples, and the direct samples are contacted directly with the PCR reaction components and the appropriate oligonucleotides. The methods are particularly useful for detecting the presence of carbapenemase in bodily fluids, such as blood and urine.

A "direct sample" is a sample that is collected from a subject and screened in a PCR reaction without isolating or culturing bacteria from the sample. The direct samples are generally only minimally processed prior to screening. In various embodiments, the samples may be lysed using any acceptable method known in the art and centrifuged to remove cellular debris. The supernatant is retained for screening. In another embodiment, the nucleic acid is pelleted, washed, and resuspended in appropriate buffer prior to screening in the PCR method.

Oligonucleotide Primers

In one embodiment of the present invention, oligonucleotide primers are provided for use in the detection of a carbapenemase antibiotic resistance gene in a sample. As used herein, a "primer" refers to a type of oligonucleotide having or containing a sequence complementary to a target polynucleotide present in or derived from the carbapenemase gene, which hybridizes to the target polynucleotide through base pairing. In one embodiment, forward and reverse primers of the invention are those comprising the nucleotide sequences set forth in SEQ ID NOs:1, 2, 4, 5, 7, 8, 14, 15, 17, 18, and 20. The term "oligonucleotide" refers to a short polynucleotide, typically less than or equal to 150 nucleotides long (e.g., between 5 and 150, preferably between 10 to 100, more preferably between 15 to 50 nucleotides in length). However, as used herein, the term is also intended to encompass longer or shorter polynucleotide chains.

The primer and probe sets of the invention are designed to detect nucleic acid molecules encoding a carbapenemase. The compositions of the invention were designed to detect at the 5', the 3', and the middle of a nucleic acid sequence encoding carbapenemase. Each of the primer and probe sets of the invention can recognize all of the known isoforms of the carbapenemase gene. The primer and probe sequences of the invention may be modified by containing additional nucleotides at the 5' or the 3' terminus. To determine the nucleotides to use for extension of the primer or probe sequence, one of skill in the art using SEQ ID NOs:10-13, which contain the full length sequence of the KPC carbapenemase genes, and Table 2, which contains the location of the primer and probe sequences within the carbapenemase sequence, can design extended primer sequences by aligning the primer and probe sequences with the carbapenemase coding sequence and determining nucleotide bases at the 5' and 3' regions of the primer or probe sequence. Likewise, the primer and probe sequences may be modified by having nucleotides substituted within the sequence. It is recognized that the primer and probe sequences must contain enough complementarity to hybridize specifically to the carbapenemase nucleic acid sequence. In this manner, at least 1, 2, 3, 4, or up to about 5 nucleotides can be substituted.

As used herein, the terms "target polynucleotide" and "target nucleic acid" refer to a polynucleotide whose presence is to be determined in a sample. In the present invention, the target nucleic acid corresponds to the nucleic acid that encodes the beta-lactamase that is capable of hydrolyzing carbapenems, carbapenemase. The nucleotide sequence of four isoforms of *Klebsiella pneumoniae* carbapenemase (KPC) are set forth in SEQ ID NOs:10-13. Any portion of the sequence may be identified by the methods of the invention. Because of the similarity of the carbapenemase sequences, the primer probe sets of the invention are capable of identifying a carbapenemase sequence in any enterobacteria.

As used herein, the term "complementary" refers to sequence complementarity between regions of two polynucleotide strands or between two regions of the same polynucleotide strand. A first region of a polynucleotide is complementary to a second region of the same or a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Fully complementary" refers to a first polynucleotide that is 100% or "fully" complementary to a second polynucleotide and thus forms a base pair at every nucleotide position. "Partially complementary" also refers to a first polynucleotide that is not 100% complementary (e.g., 90%, or 80% or 70% complementary) and contains mismatched nucleotides at one or more nucleotide positions.

As used herein, the term "hybridization" is used in reference to the pairing of complementary (including partially complementary) polynucleotide strands. Hybridization and the strength of hybridization (i.e., the strength of the association between polynucleotide strands) is impacted by many factors well known in the art including the degree of complementarity between the polynucleotides, stringency of the conditions involved affected by such conditions as the concentration of salts, the melting temperature (Tm) of the formed hybrid, the presence of other components (e.g., the presence or absence of polyethylene glycol), the molarity of the hybridizing strands and the G:C content of the polynucleotide strands. In one embodiment, the primers are designed such that the Tm of one primer in the set is within 2° C. of the Tm of the other primer in the set. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The primers of the present invention can be prepared using techniques known in the art, including, but not limited to, cloning and digestion of the appropriate sequences and direct chemical synthesis.

Chemical synthesis methods that can be used to make the primers of the present invention, include, but are not limited to, the phosphotriester method described by Narang et al. (1979) *Methods in Enzymology* 68:90, the phosphodiester method disclosed by Brown et al. (1979) *Methods in Enzymology* 68:109, the diethylphosphoramidate method disclosed by Beaucage et al. (1981) *Tetrahedron Letters* 22:1859, and the solid support method described in U.S. Pat. No. 4,458,066. The use of an automated oligonucleotide synthesizer to prepare synthetic oligonucleotide primers of the present invention is also contemplated herein. Additionally, if desired, the primers can be labeled using techniques known in the art and described below.

Oligonucleotide Probes

One or more of the oligonucleotide primers of the present invention may be used with or may comprise one or more probe sequences. The probes may be separate from the oligonucleotide primers ("bimolecular probes"), or, attached to the oligonucleotide primer ("unimolecular probes" or "tailed probes"). See, for example, the self-probing sequences (e.g., SCORPIONS™ primers, also referred to as "tailed probes") described in Whitcombe et al. (1999) *Nature Biotechnol.* 17:804-807 and U.S. Pat. No. 6,326,145, both of which are herein incorporated by reference in their entirety.

As used herein, the term "probe" refers to a polynucleotide that forms a hybrid structure with a primer extension product due to complementarity of at least one sequence in the probe with a sequence in the primer extension product. By "primer extension product" is intended the nucleic acid product that results from polymerase-based extension (using the target nucleic acid as a template) of the oligonucleotide primer comprising the sequences disclosed herein as SEQ ID NOs:1, 2, 4, 5, 7, 8, 14, 15, 17, 18, and 20. The polynucleotide regions of the probe can be composed of DNA and/or RNA and/or synthetic nucleotide analogs. Preferably, the probe does not contain a sequence complementary to the oligonucleotide primer sequence(s) described above. The probe of the present invention is ideally less than or equal to about 50 nucleotides in length, for example less than or equal to about 40, about 30, about 20, or less than about 10 nucleotides in length. Preferably, the probe sequences of the invention are the sequences disclosed herein as SEQ ID NOs:3, 6, 9, 16, and 19.

As used herein, "Tm" and "melting temperature" are interchangeable terms which are the temperature at which 50% of a population of double-stranded polynucleotide molecules becomes dissociated into single strands. The equation for calculating the Tm of polynucleotides is well known in the art. For example, the Tm may be calculated by the following equation: $Tm=69.3+0.41\times(G+C)\%-650/L$, wherein L is the length of the probe in nucleotides. The Tm of a hybrid polynucleotide may also be estimated using a formula adopted from hybridization assays in 1 M salt, and commonly used for calculating Tm for PCR primers: [(number of A+T)×2° C.+ (number of G+C)×4° C.], see, for example, Newton et al. (1997) *PCR* (2nd ed; Springer-Verlag, New York). Other more sophisticated computations exist in the art, which take structural as well as sequence characteristics into account for the calculation of Tm. A calculated Tm is merely an estimate; the optimum temperature is commonly determined empirically.

Labeling

The primers and/or probes of the present invention can further include one or more labels to facilitate monitoring of amplification reactions. As used herein, the term "label" or "labeled" refers to any atom or moiety that can be used to provide a detectable (preferably, quantifiable) signal, and which can be attached to a polynucleotide, oligonucleotide primer, or probe. A wide variety of labels and conjugation techniques, including direct and indirect labeling, are known and are reported extensively in both the scientific and patent literature. Examples of labels that can be used include radionucleotides, enzymes, substrates, cofactors, inhibitors, fluorescent moieties, intercalators, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241, herein incorporated by reference in their entirety.

III. Methods

Further provided herein are rapid and sensitive methods for detection of a bacterium having carbapenem resistance in a sample. The methods are useful for diagnosing a subject with carbapenem resistance, as well as developing a treatment regimen appropriate for a subject having a bacterial infection where the treatment is determined based on the presence or absence of carbapenem resistance.

The methods comprise a PCR, particularly a QPCR, based method of amplification and detection of carbapenemase using the primers and probes described herein. In various embodiments, the methods disclosed herein are capable of detecting the presence of carbapenemase at a concentration of bacteria that is within physiological ranges (i.e., the concentration of bacteria in a sample collected from a subject infected with the bacteria). Thus, a sample can be directly screened without the need for isolating, concentrating, or expanding (e.g., culturing) the bacterial population in order to detect the presence of carbapenemase. In various embodiments, the methods disclosed herein are capable of detecting the presence of carbapenemase from a sample that has a concentration of bacteria of about $1\times10^3$ CFU/ml, about $1\times10^4$ CFU/ml, about $1\times10^5$ CFU/ml, or about $1\times10^6$ CFU/ml.

Polymerase-Based Amplification

Numerous different PCR or QPCR protocols are known in the art and exemplified herein below and can be directly applied or adapted for use using the presently described compositions for the detection of carbapenemase in a sample. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence that is the amplification product). The amplification cycle is repeated to increase the concentration of the single target polynucleotide sequence. The reaction can be performed in any thermocycler commonly used for PCR. However, preferred are cyclers with real-time fluorescence measurement capabilities, for example, SMART-CYCLER® (Cepheid, Sunnyvale, Calif.), ABI PRISM 7700® (Applied Biosystems, Foster City, Calif.), ROTOR-GENE™ (Corbett Research, Sydney, Australia), LIGHTCY-CLER® (Roche Diagnostics Corp, Indianapolis, Ind.), ICY-CLER® (Biorad Laboratories, Hercules, Calif.) and MX4000® (Stratagene, La Jolla, Calif.).

Quantitative PCR (QPCR) (also referred as real-time PCR) is preferred under some circumstances because it provides not only a quantitative measurement, but also reduced time and contamination. As used herein, "quantitative PCR" (or "real time QPCR") refers to the direct monitoring of the progress of a PCR amplification as it is occurring without the need for repeated sampling of the reaction products. In QPCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence (herein referred to as cycle threshold or "CT") varies directly with the concentration of amplifiable targets at the beginning of the PCR process, enabling a measure of signal intensity to provide a measure of the amount of target nucleic acid in a sample in real time.

In a preferred embodiment, a labeled probe is used to detect the extension product generated by PCR amplification. Any probe format utilizing a labeled probe comprising the sequences of the invention may be used, e.g., such as SCORPIONS™ probes, sunrise probes, TAQMAN® probes, or molecular beacon probes as is known in the art or described elsewhere herein.

PCR Conditions

Methods for setting up a PCR reaction are well known to those skilled in the art. The reaction mixture minimally comprises template nucleic acid (except in the case of a negative control as described below) and oligonucleotide primers and/or probes in combination with suitable buffers, salts, and the like, and an appropriate concentration of a nucleic acid polymerase. As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template until synthesis terminates. An appropriate concentration includes one that catalyzes this reaction in the presently described methods. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

In addition to the above components, the reaction mixture of the present methods includes primers, probes, and deoxyribonucleoside triphosphates (dNTPs). Usually the reaction mixture will further comprise four different types of dNTPs corresponding to the four naturally occurring nucleoside bases, i.e., dATP, dTTP, dCTP, and dGTP. In the methods of the invention, each dNTP will typically be present in an amount ranging from about 10 to 5000 µM, usually from about 20 to 1000 µM, about 100 to 800 µM, or about 300 to 600 µM.

The reaction mixture prepared in the first step of the methods of the invention further includes an aqueous buffer medium that includes a source of monovalent ions, a source of divalent cations, and a buffering agent. Any convenient source of monovalent ions, such as potassium chloride, potassium acetate, ammonium acetate, potassium glutamate, ammonium chloride, ammonium sulfate, and the like may be employed. The divalent cation may be magnesium, manganese, zinc, and the like, where the cation will typically be magnesium. Any convenient source of magnesium cation may be employed, including magnesium chloride, magnesium acetate, and the like. The amount of magnesium present in the buffer may range from 0.5 to 10 mM, and can range from about 1 to about 6 mM, or about 3 to about 5 mM. Representative buffering agents or salts that may be present in the buffer include Tris, Tricine, HEPES, MOPS, and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, for example, about pH 6.0, 6.5, 7.0, 7.5, 8.0, 8.5, 9.0, or 9.5. Other agents that may be present in the buffer medium include chelating agents, such as EDTA, EGTA, and the like.

In preparing the reaction mixture, the various constituent components may be combined in any convenient order. For example, the buffer may be combined with primer, polymerase, and then template nucleic acid, or all of the various constituent components may be combined at the same time to produce the reaction mixture.

Alternatively, commercially available premixed reagents can be utilized in the methods of the invention according to the manufacturer's instructions, or modified to improve reaction conditions (e.g., modification of buffer concentration, cation concentration, or dNTP concentration, as necessary), including, for example, TAQMAN® Universal PCR Master Mix (Applied Biosystems), OMNIMIX® or SMARTMIX® (Cepheid), IQ™ Supermix (Bio-Rad Laboratories), LIGHTCYCLER® FastStart (Roche Applied Science, Indianapolis, Ind.), or BRILLIANT® QPCR Master Mix (Stratagene, La Jolla, Calif.).

Following preparation of the reaction mixture, the reaction mixture is subjected to primer extension reaction conditions ("conditions sufficient to provide polymerase-based nucleic acid amplification products"), i.e., conditions that permit for polymerase-mediated primer extension by addition of nucleotides to the end of the primer molecule using the template strand as a template. In many embodiments, the primer extension reaction conditions are amplification conditions, which conditions include a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20, and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double-stranded or hybridized nucleic acid present in the reaction mixture to dissociate. For denaturation, the temperature of the reaction mixture will usually be raised to, and maintained at, a temperature ranging from about 85 to 100° C., usually from about 90 to 98° C., and more usually from about 93 to 96° C., for a period of time ranging from about 3 to 120 sec, usually from about 3 sec.

Following denaturation, the reaction mixture will be subjected to conditions sufficient for primer annealing to template nucleic acid present in the mixture (if present), and for polymerization of nucleotides to the primer ends in a manner such that the primer is extended in a 5' to 3' direction using the nucleic acid to which it is hybridized as a template, i.e., conditions sufficient for enzymatic production of primer extension product. In this embodiment, the annealing and extension processes occur in the same step. The temperature to which the reaction mixture is lowered to achieve these conditions will usually be chosen to provide optimal efficiency and specificity, and will generally range from about 50 to 75° C., usually from about 55 to 70° C., and more usually from about 60 to 68° C., more particularly around 60° C. Annealing conditions will be maintained for a period of time ranging from about 15 sec to 30 min, usually from about 20 sec to 5 min, or about 30 sec to 1 minute, or about 30 seconds.

This step can optionally comprise one of each of an annealing step and an extension step with variation and optimization of the temperature and length of time for each step. In a two-step annealing and extension, the annealing step is allowed to proceed as above. Following annealing of primer to template nucleic acid, the reaction mixture will be further subjected to conditions sufficient to provide for polymerization of nucleotides to the primer ends as above. To achieve polymerization conditions, the temperature of the reaction mixture will typically be raised to or maintained at a temperature ranging from about 65 to 75° C., usually from about 67 to 73° C. and maintained for a period of time ranging from about 15 sec to 20 min, usually from about 30 sec to 5 min.

The above cycles of denaturation, annealing, and polymerization may be performed using an automated device, typically known as a thermal cycler. Thermal cyclers that may be employed are described elsewhere herein as well as in U.S. Pat. Nos. 5,612,473; 5,602,756; 5,538,871; and 5,475,610; the disclosures of which are herein incorporated by reference.

The methods of the invention can also be used in non-PCR based applications to detect a target nucleic acid sequence, where such target may be immobilized on a solid support. Methods of immobilizing a nucleic acid sequence on a solid support are known in the art and are described in Ausubel et al., eds. (1995) *Current Protocols in Molecular Biology* (Greene Publishing and Wiley-Interscience, NY), and in protocols provided by the manufacturers, e.g., for membranes: Pall Corporation, Schleicher & Schuell; for magnetic beads: Dynal; for culture plates: Costar, Nalgenunc; for bead array platforms: Luminex and Becton Dickinson; and, for other supports useful according to the invention, CPG, Inc.

The person skilled in the art of nucleic acid amplification knows the existence of other rapid amplification procedures such as ligase chain reaction (LCR), transcription-based amplification systems (TAS), self-sustained sequence replication (3SR), nucleic acid sequence-based amplification (NASBA), strand displacement amplification (SDA) and branched DNA (bDNA) (Persing et al. (1993) Diagnostic Molecular Microbiology Principles and Applications (American Society for Microbiology, Washington, D.C.). The scope of this invention is not limited to the use of amplification by PCR, but rather includes the use of any rapid nucleic acid amplification methods or any other procedures that may be useful with the sequences of the invention for the detection and/or quantification of the carbapenemase antibiotic resistance gene.

Further, variations on the exact amounts of the various reagents and on the conditions for the PCR or other suitable amplification procedure (e.g., buffer conditions, cycling times, etc.) that lead to similar amplification or detection/quantification results are known to those of skill in the art and are considered to be equivalents. In one embodiment, the subject QPCR detection has a sensitivity of detecting fewer than 50 copies (preferably fewer than 25 copies, more preferably fewer than 15 copies, still more preferably fewer than 10 copies) of target nucleic acid (i.e., carbapenemase nucleic acid) in a sample. In one embodiment, a hot-start PCR reaction is performed (e.g., using a hot start Taq DNA polymerase) so as to improve PCR reaction by decreasing background from non-specific amplification and to increase amplification of the desired extension product.

Controls

The PCR or QPCR reaction of the present invention may contain various controls. Such controls should include a "no template" negative control, in which primers, buffer, enzyme(s) and other necessary reagents (e.g., magnesium chloride, nucleotides) are cycled in the absence of added test sample. A positive control including a known target nucleic acid should also be run in parallel. Both positive control and negative control may be included in the amplification reaction. A single reaction may contain either a positive control, a negative control, or a sample template, or a single reaction may contain both a sample template and a positive control.

In addition to "no template" controls, negative controls can also include amplification reactions with non-specific target nucleic acid included in the reaction, or can be samples prepared using any or all steps of the sample preparation (from nucleic acid extraction to amplification preparation) without the addition of a test sample (e.g., each step uses either no test sample or a sample known to be free of carbapenemase).

Positive and negative controls are useful for setting the parameters within which a test sample will be classified as having or not having carbapenem resistance. For example, in a QPCR reaction, the cycle threshold at which carbapenemase is detected in a positive control sample can be used to set the threshold for classifying a sample as "positive," and the cycle threshold at which carbapenemase is detected in a negative control sample can be used to set the threshold for classifying a sample as "negative." The CT from a single reaction may be used for each control, or the median or mean of replicate samples may be used. In yet another embodiment, historical control values may be used. The minimum level of detection for each of the negative and the positive controls is typically set at the lower end of the 95% confidence interval of the mean CT across multiple reactions. This value can be adjusted depending on the requirements of the diagnostic assay.

Confirmation of Primer Extension Product

If desired, the identity of the primer extension or amplification product can be confirmed using standard molecular techniques including (for example) a Southern blot assay. In a Southern blot assay, the amplification products are separated by electrophoresis, transferred to a membrane (i.e., nitrocellulose, nylon, etc.), reacted with an oligonucleotide probe or any portion of the nucleic acid sequence of interest. The probe is then modified to enable detection. The modification methods can be the incorporation of a radiolabeled nucleotide or any number of non-radioactive labels (such as biotin).

The oligonucleotide probe used in the Southern blot assay is derived from the nucleic acid sequence and hence is specific for this carbapenemase antibiotic resistance gene, and can be a probe comprising the sequence set forth in SEQ ID NO:3, 6, 9, 16, or 19. The probe used in the Southern blot assay can be prepared using routine, standard methods. For example, the probe can be isolated, cloned, and restricted using routine techniques known in the art or can be made using the chemical synthesis methods described previously herein.

Alternatively, the amplification products can be detected using dot blot analysis. Dot blot analysis involves adhering an oligonucleotide probe (such as the one described previously) to a nitrocellulose or solid support such as, but not limited to, a bead (such as, but not limited to, polystyrene beads, magnetic beads, or non-magnetic beads, etc.), walls of a reaction tray, strips (such as, but not limited to, nitrocellulose strips), a test tube. The sample containing the labeled amplification product is added, reacted, washed to removed unbound sample, and a labeled, amplified product attached to the probe is visualized using routine techniques known in the art. A more stringent way to verify the primer extension product or amplification product is through direct sequencing using techniques well known in the art.

Kits

The present invention lends itself readily to the preparation of "kits" containing the elements necessary to carry out the methods of the invention. Such a kit may comprise a carrier being compartmentalized to receive in close confinement therein one or more containers, such as tubes or vials. One of the containers may contain at least one unlabeled or detectably labeled DNA primer of the invention. The labeled DNA primer or primers may be present in lyophilized form or in an appropriate buffer as necessary. One or more containers may contain one or more enzymes or reagents to be utilized in PCR reactions. These enzymes may be present by themselves or in admixtures, in lyophilized form or in appropriate buffers. Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The kits according to the present invention will comprise at least: (a) a labeled oligonucleotide, where the kit includes two or more distinguishable oligonucleotides, e.g., that hybridize to a nucleotide sequence encoding a carbapenemase; and (b) instructions for using the provided labeled oligonucleotide(s) in a high fidelity amplification, e.g., PCR, reaction. In one embodiment the two distinguishable oligonucleotides will be selected from the group consisting of SEQ ID NOS:1-9 and 14-20.

The subject kits may further comprise additional reagents that are required for or convenient and/or desirable to include in the reaction mixture prepared during the methods of the invention, where such reagents include: one or more polymerases; an aqueous buffer medium (either prepared or present in its constituent components, where one or more of the components may be premixed or all of the components may be separate), and the like.

The various reagent components of the kits may be present in separate containers, or may all be precombined into a reagent mixture for combination with template nucleic acid.

In addition to the above components, the kits will further include instructions for practicing the methods of the present invention. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address that may be used via the internet to access the information at a removed site. Any convenient means may be present in the kits.

The following examples are offered by way of illustration and not by way of limitation.

EXPERIMENTAL

Materials and Methods

References (1)-(6) referred to below are listed at the end of the Experimental Section.

Bacterial strains: Carbapenem-resistant *Klebsiella* and *E. coli* were identified by broth microdilution as described by CLSI from the BD ID/AST microbial bank (1). Wild-type (Ampicillin sensitive) *E. coli* ATCC 25922 (Strain ID 300960) was used through out the experiments as a negative control. Three strains previously determined to contain KPC-1, KPC-2, and KPC-3 (Strain ID 301916=KPC-1, 301917=KPC-2, 301918=KPC-3) were used as positive controls (4). ESBL positive *Klebsiella* and *E. coli* were also screened to demonstrate the specificity of the Real-Time assays. ESBL positive strains were identified using the CLSI recommended broth microdilution assay (2). Prior to any processing or extraction, all strains were streaked out on Trypticase Soy Agar (TSA) plates containing 5% Sheep red blood cells (BD Diagnostic Systems, Sparks, Md.) and grown at 35° C. overnight.

Antimicrobial susceptibility testing: Antimicrobial susceptibility testing was performed using Mueller-Hinton broth (BD Diagnostic Systems, Sparks, Md.) as described by CLSI (1). Antimicrobial powders were acquired from the following companies; Ampicillin (Amp) and Cefotaxime (CTX) (Sigma Chemical Co., St. Louis, Mo.), Ceftazidime (CAZ) (Eli Lilly, Indianapolis, Ind.), Clavulanic acid (Smith-Kline, King of Prussia, Pa.), Imipenem (IPM) (Merck & Co., Rahway, N.J.).

DNA extraction and normalization: Bacterial DNA isolation was done using a standard heat lysis protocol. In this protocol, a portion of a colony from a TSA isolation plate was placed into 50 µl of molecular biology grade water. The samples were then incubated at 95° C. while shaking at 800 rpms for 10 minutes (min). DNA was recovered by a brief centrifugation step, 14,000 rpms (20,800×g) for 5 min. The supernatant containing the DNA was removed and placed into a clean tube. Samples underwent spectrophotometry and the nucleic acids were normalized to 100 ng/µl in 10 mMTris-HCL with 1 mM EDTA (TE) buffer at pH 8.0. DNA purity was determined by analyzing the 260/280 absorbance ratio; pure DNA has a ratio>1.7.

Real Time PCR protocol: All purified DNA (100 ng/µl) was diluted at least 1/20 prior to PCR analysis to dilute out any inhibitory proteins present in the heat lysed samples. A 5 ng aliquot of the DNA sample was placed into a 20 µl PCR master mix containing 250 nM of each primer, 125 nM of the dual-labeled probe and the TaqMan® Universal Fast PCR Master Mix (Applied Biosystems, Foster City, Calif.). Sequences for primers and probes used in the real-time assays can be found in Table 2. All primers and probes were synthesized by Integrated DNA Technologies, Inc., under the direction of this project. Dual-labeled hydrolysis probes were synthesized with 5' 6-FAM™/3' BHQ-1™ and 2×HPLC purified. Samples were run on Applied Biosystems (ABI) 7500 Fast Real-Time PCR System (Applied Biosystems, Foster City, Calif.) using a 2 stage 2 step PCR program in which there is a 20 second (sec) enzyme activation stage and a 2 step PCR stage consisting of a 3 sec 95° C. denaturing step and a 30 sec 60° C. annealing/extension step for 40 cycles. The average run time for the PCR program was 35 min.

Sequencing: Amplicon Sequencing was performed using primers described in Yigit et al. 2001 (3) and Bratu et al. 2005 (5) to validate the KPC positive strains identified in the Real-Time PCR assay. A 100 ng aliquot of the DNA sample was placed into a 15 µl PCR master mix containing 0.2 pmol of each primer and the Qiagen® Multiplex PCR Master Mix (Qiagen, Valencia, Calif.). The reactions were amplified in a MJ Research PTC-200 thermal cycler (BioRad, Hercules, Calif.) using the cycling parameters described by the vendor (Qiagen). The PCR reactions were cleaned up according to the ExoSap-IT® (USB Corporation, Cleveland, Ohio) protocol. Sequencing reactions and cycling parameters were performed according to the ABI BigDye® Terminator v1.1 Cycle Sequencing kit (Applied Biosystems, Foster City, Calif.). Sequencing reaction products were purified using the DyEx™ 2.0 Spin Kit (Qiagen, Valencia, Calif.) according to manufacturer supplied protocol and analyzed on an ABI 3130 Genetic Analyzer (Applied Biosystems, Foster City, Calif.). The sequences obtained from the KPC amplicon sequencing were compared to the non-redundant sequences in GenBank using the BLAST algorithm from National Center for Biotechnology Information (NCBI).

Results

KPC alignment and assay design: KPC and its' associated variants were acquired from NCBI. All of the unique KPC variants were aligned using the Clustal W algorithm in the DNASTAR (DNASTAR, Inc. Madison, Wis.) sequence analysis software to reveal all of the nucleotide variants associated with the KPC isoforms. All of the KPC variants identified in the alignment are listed in Table 1 along with their GenBank accession numbers and the reservoir species. Aligned sequences were then used as a reference for the primer and probe design. The real-time assays were specifically chosen for their ability to recognize all KPC variants. The majority of the primers and probes from the real-time assays do not overlap the known KPC variants with the exception of the KPC-758 assay. The reverse primer in the KPC-758 assay does overlap with the KPC-3 variant at nucleotide position 814. The KPC-3 variant is detected with the KPC-758 assay with no apparent loss in sensitivity (see CT values in Table 4 below). Primers and probes were designed with the aid of Primer Express v3 (Applied Biosystems, Foster City, Calif.) with the criteria that all primers had to be within 2 degrees of each other and within 2 degrees of the optimal Tm (melting temperature) of 60° C. The Tm for the probes was 10 degrees higher than the primer pairs to increase the specificity of probe annealing (Table 2). The KPC real-time primers and probes were compared to the non-redundant sequences in GenBank using the BLAST algorithm from NCBI. All the real-time assays matched the available GenBank KPC sequences with >100% coverage and >100% sequence identity and did not have any significant identity to any other gene in the database.

TABLE 1

KPC nucleotide variants. Sequences were downloaded from GenBank, aligned using Clustal W algorithm in DNASTAR (DNASTAR, Inc. Madison, WI) to identify the specific nucleotide variations and locations associated with each KPC isoform. Also noted are some of the reservoir species for the KPC gene.

| Isoform | Nucleotide Position* | Base Change** | GenBank Accession | Bacterium |
|---|---|---|---|---|
| KPC-1 | 520 | G→A | AF297554 | Klebsiella pneumoniae |
| KPC-3 | 814 | C→T | AF395881 | Klebsiella pneumoniae |
| KPC-4 | 308 | C→G | AY700571 | Enterobacter species |
| KPC-4 | 716 | T→G | AY700571 | Enterobacter species |
| KPC-2*** | | | AY034847 | Klebsiella pneumoniae |

*Nucleotide position is based on the open reading frame or coding sequence of the KPC gene.
**Base change is a change compared to the consensus base at that position.
***KPC-2 variant is determined by the lack of any of the above mentioned changes.

TABLE 2

Real-time assays for KPC. Real-time assays were specifically chosen for their ability to recognize all KPC variants. Primers were designed to be within 2 degrees of each other and within 2 degrees of the optimal Tm of 60° C. and the Tm for the probes were designed to be 10 degrees higher than the primer pairs. "Start" and "Stop" refer to the corresponding nucleotide position within the KPC coding sequence (See, SEQ ID NOs: 10-13).

| | Sequence | Start | Stop | Tm |
|---|---|---|---|---|
| Assay: KPC-87 | | | | |
| Forward Primer | CGCGGAACCATTCGCTAA (SEQ ID NO: 1) | 87 | 104 | 59 |
| Reverse Primer | CGGTATCCATCGCGTACACA (SEQ ID NO: 2) | 154 | 135 | 59 |
| Probe | CTCGAACAGGACTTTGGCGGCTCC (SEQ ID NO: 3) | 106 | 129 | 70 |
| Assay: KPC-289 | | | | |
| Forward Primer | GGCAAAAATGCGCTGGTT (SEQ ID NO: 4) | 289 | 306 | 58 |
| Reverse Primer | GCCACCGTCATGCCTGTT (SEQ ID NO: 5) | 356 | 339 | 59 |
| Probe | CGTGGTCACCCATCTCGGAAAAATATCTGA (SEQ ID NO: 6) | 307 | 336 | 69 |
| Assay: KPC-758 | | | | |
| Forward Primer | GGCGCGCACCTATTGTGT (SEQ ID NO: 7) | 758 | 775 | 59 |
| Reverse Primer | CGCTGTGCTTGTCATCCTTGT (SEQ ID NO: 8) | 820 | 800 | 60 |
| Probe | CCGTCTACACCCGGGCGCCT (SEQ ID NO: 9) | 779 | 798 | 69 |
| Assay: KPC-91 | | | | |
| Forward Primer | GAACCATTCGCTAAACTCGAACA (SEQ ID NO: 14) | 91 | 113 | 59 |
| Reverse Primer | CGGTATCCATCGCGTACACA (SEQ ID NO: 2) | 154 | 135 | 59 |
| Probe | ACTTTGGCGGCTCC (SEQ ID NO: 3) | 116 | 129 | 69 |

TABLE 2-continued

Real-time assays for KPC. Real-time assays were specifically chosen for their ability to recognize all KPC variants. Primers were designed to be within 2 degrees of each other and within 2 degrees of the optimal Tm of 60° C. and the Tm for the probes were designed to be 10 degrees higher than the primer pairs. "Start" and "Stop" refer to the corresponding nucleotide position within the KPC coding sequence (See, SEQ ID NOs: 10-13).

| Sequence | Start | Stop | Tm |
|---|---|---|---|
| Assay: KPC-289 | | | |
| Forward Primer GGCAAAAATGCGCTGGTT (SEQ ID NO: 4) | 289 | 306 | 58 |
| Reverse Primer CCGTCATGCCTGTTGTCAGA (SEQ ID NO: 15) | 352 | 333 | 59 |
| Probe CCCATCTCGGAAAAA (SEQ ID NO: 16) | 316 | 330 | 69 |
| Assay: KPC-372 | | | |
| Forward Primer CGCCGTGCAATACAGTGATAAC (SEQ ID NO: 17) | 372 | 393 | 59 |
| Reverse Primer CGGGCCGCCCAACT (SEQ ID NO: 18) | 432 | 419 | 59 |
| Probe CCGCCAATTTGTTGCTGA (SEQ ID NO: 19) | 398 | 415 | 70 |
| Assay: KPC-754 | | | |
| Forward Primer ACTGGGCGCGCACCTA (SEQ ID NO: 20) | 754 | 769 | 58 |
| Reverse Primer CGCTGTGCTTGTCATCCTTGT (SEQ ID NO: 8) | 820 | 800 | 60 |
| Probe CCGTCTACACCCGGGCGCC (SEQ ID NO: 9) | 779 | 797 | 69 |

Screening for Carbapenem-hydrolyzing and ESBL-producing strains: The BD ID/AST Microbial Bank was screened for carbapenem-resistant *Klebsiella* and *E. coli* with broth microdilution as described by CLSI (2). *Klebsiella* spp. and *E. coli* were chosen because they are the primary reservoir species for the plasmid-borne KPC gene. The minimum inhibition concentrations (MIC's) of IPM were evaluated within a range of 2-16 μg/ml based on standard microbroth dilution, with ≧16 μg/ml being considered as resistant to IPM (2). Three out of the twenty-four strains in Table 3 (shown as underlined) were resistant (≧16 μg/ml) to IPM according to the CLSI standard.

Additional *Klebsiella* spp. and *E. coli* strains that were not IPM resistant but ESBL positive were screened due to reports in the literature that suggest that KPC-producing isolates are associated with a positive ESBL CLSI confirmatory test (6) and that some KPC-producing isolates have been found to be below the IPM resistance point of ≧16 μg/ml (6). These additional ESBL strains were included to demonstrate the sensitivity and specificity of the real-time assays.

ESBL positive strains were identified using the CLSI recommended broth microdilution assay (2). Briefly, this broth microdilution assay has a two-fold dilution scheme between a defined range of the antimicrobial agent. For example, where the defined range of the antimicrobial agent is 2-16 μg/ml, the two-fold dilution between wells is represented by 0.25, 0.5, 1, 2, 4, 8, and 16 μg/ml. To identify ESBL positive strains, growth is evaluated in wells containing the antimicrobial agent of interest at these various two-fold dilutions across the defined range either alone or in combination with Clavulanic acid in order to determine the MIC for the antimicrobial agent alone or in combination with Clavulanic acid. The addition of Clavulanic acid to an antimicrobial agent can reduce the MIC of the agent, for example, such that microbial growth is inhibited in a well containing 1 μg/ml of the agent+ Clavulanic acid as opposed to being inhibited in a well containing 8 μg/ml of the agent alone. This particular example would equate to a reduction in MIC by 3 wells (which have a 2-fold dilution between each of these wells), and this type of reduction in MIC would warrant the microbe being called ESBL positive. Thus, a ≧3 two-fold concentration decrease in an MIC for an antimicrobial agent tested in combination with Clavulanic acid versus its MIC when tested alone is indicative of the microbe being ESBL positive (e.g., CAZ MIC=8 μg/ml; CCZ (Clavulanic acid+Ceftazidime (CCZ)) MIC=1 μg/ml). Eleven out of the twenty-four strains in Table 3 are ESBL positive according to the CLSI standard (see Table 3, within the column for each assay, where results indicating an ESBL positive strain are denoted with an asterisk). A wild-type *E. coli* Strain ID 300960 was also screened and used as a negative control for all of the real-time assays.

TABLE 3

Antimicrobial susceptibility testing. Antimicrobial susceptibility testing was performed using Mueller-Hinton broth (BD Diagnostic Systems, Sparks, MD.) as described by CLSI (1). IPM resistant strains (≧16 μg/ml) are underlined and ESBL positive strains (using CLSI standards) are denoted with an asterisk.

| Strain ID | Bacterium | Amp | CTX | CCX | CAZ | CCZ | IPM |
|---|---|---|---|---|---|---|---|
| 300960 | ESCCOL | <=0.25 | <=0.25 | <=0.25 | <=0.5 | <=0.25 | <=0.25 |
| 300967 | KLEOXY | >32 | >64 | >64 | =128 | =128 | ≧16 |

TABLE 3-continued

Antimicrobial susceptibility testing. Antimicrobial susceptibility testing was performed using Mueller-Hinton broth (BD Diagnostic Systems, Sparks, MD.) as described by CLSI (1). IPM resistant strains (≧16 μg/ml) are underlined and ESBL positive strains (using CLSI standards) are denoted with an asterisk.

| Strain ID | Bacterium | Amp | CTX | CCX | CAZ | CCZ | IPM |
|---|---|---|---|---|---|---|---|
| 300996 | KLEPNEP | >32 | =2* | =0.5* | =4* | =0.5* | =8 |
| 301008 | KLEPNEP | =16 | <=0.25 | <=0.25 | <=0.25 | <=0.25 | <=2 |
| 301888 | ESCCOL | >32 | =32* | =1* | =64* | =2* | =4 |
| 301891 | KLEPNEP | >32 | =4 | =4 | =16 | =16 | <=2 |
| 301892 | ESCCOL | >32 | =32* | =4* | =64* | =4* | =4 |
| 301894 | ESCCOL | >32 | =16* | <=0.25* | >128* | =2* | <=2 |
| 301896 | ESCCOL | >32 | =64* | <=0.25* | >128* | =1* | <=2 |
| 301898 | KLEPNEP | >32 | >64 | >64 | >128 | >128 | =4 |
| 301899 | KLEPNEP | >32 | >64 | >64 | >128 | >128 | =4 |
| 301905 | ESCCOL | >32 | >64 | =16 | =32 | =16 | =8 |
| 301916 | KLEPNEP | >32 | >64 | >64 | >128 | >128 | =8 |
| 301917 | KLEPNEP | >32 | =32* | =0.5* | =4* | =2* | =8 |
| 301918 | ESCCOL | >32 | >64 | >64 | >128 | >128 | =16 |
| 301919 | KLEPNEP | >32 | =16* | <=0.25* | =32* | <=0.25* | <=2 |
| 301920 | KLEPNEP | >32 | >64* | <=0.25* | =64* | <=0.25* | <=2 |
| 301921 | ESCCOL | >32 | >64* | <=0.25* | =32* | <=0.25* | <=2 |
| 301922 | ESCCOL | >32 | >64* | <=0.25* | =16* | =0.5* | <=0.25 |
| 303364 | ESCCOL | >32 | =32 | =16 | =128 | =64 | <=2 |
| 303365 | ESCCOL | >32 | >64* | <=0.25* | >128* | =1* | <=2 |
| 303369 | ESCCOL | >32 | =32 | =8 | =64 | =64 | <=2 |
| 303375 | KLEPNEP | >32 | =32 | =64 | =64 | =64 | <=2 |
| 303990 | KLEOXY | >32 | >64 | >64 | =128 | =128 | =16 |

ESCCOL = *E. coli*
KLEOXY = *Klebsiella oxytoca*
KLEPNEP = *Klebsiella pneumoniae*
CCX = Clavulanic acid + Cefotaxime
CCZ = Clavulanic acid + Ceftazidime KPC Real-Time PCR assays: Total DNA was isolated from the strains listed in Table 3 using the heat lysis protocol outlined in the material and methods. The total DNA was diluted at least 1/20 prior to real-time PCR analysis to dilute out any inhibitory proteins present in the heat lysed samples. An aliquot of the DNA sample was placed into a PCR master mix containing each primer, the dual-labeled probe and the Taq-Man® Universal Fast PCR Master Mix (Applied Biosystems, Foster City, Calif.). The sequences of the primers and probes used in the real-time assays can be found in Table 2. Samples were run on Applied Biosystems (ABI) 7500 Fast Real-Time PCR System (Applied Biosystems, Foster City, Calif.) using a 2 stage 2 step PCR program for 40 cycles. All assays were run in duplicate and cycle threshold (CT) values for the samples were calculated using the ABI Sequence Detection software v1.3.1 (Applied Biosystems, Foster City, Calif.) following user defined baseline and CT. CT was set in the linear or exponential phase of the curves for the positive controls. The baseline for the analysis was set in a region ($3^{rd}$-$12^{th}$ cycle), which did not have any sample that crossed the CT. To determine a CT range for a positive or negative call, the positive and negative controls were analyzed. The ranges (i.e., Min CT Call or Max CT Call) seen in Table 4 were calculated to be +/−6 standard deviations (StdDev) from the average CT, which was calculated from the positive or negative controls using all the KPC assays (87, 289, and 758). These positive and negative call ranges were used to score all of the strains.

TABLE 4

Call range for the KPC real-time assays. All assays were run in duplicate and CT values for all samples were calculated using the ABI Sequence detection software following user defined background and CT. Both the Min CT Call and Max CT Call were calculated to be +/−6 StdDev from the average CT (from all the KPC assays) of either the positive or negative controls.

| Strain ID | Avg CT | StdDev | 6 StdDev | Min Ct Call | Max Ct Call |
|---|---|---|---|---|---|
| Negative control | | | | | |
| 300960-ATCC-25922 | 29.5 | 0.9 | 5.3 | 24.1 | 34.8 |
| Positive controls | | | | | |
| 301916-KPC-1 | 16.4 | 0.6 | 3.6 | 12.8 | 20.0 |
| 301917-KPC-2 | 18.5 | 0.5 | 3.2 | 15.3 | 21.7 |
| 301918-KPC-3 | 16.2 | 0.8 | 5.0 | 11.2 | 21.3 |

All replicate positive reactions within a given KPC assay were 0.3 StdDev of each other.

Table 5 contains the calls for all 24 strains tested; these calls were made using the average CT value calculated across all the KPC assays for a given strain. A total of 10 strains were called positive out of the 24 strains tested. In Table 6, the average (Avg) Intra-CT distance (max positive/negative Avg CT−min positive/negative Avg CT), the average CT, and the average Inter-CT distance (positive Avg CT−negative Avg CT) were calculated for all positive and negative strains using the calls and average (Avg) CT values from Table 5. The Avg Intra-CT distance among the positive strains was within 4.4 CTs of each other and the Avg Inter-CT distance was 14.4 CTs less than the negative controls. These results indicate these assays can distinguish a positive strain from a negative strain over many orders of magnitude (to be exact $2^{14.4}$), assuming the assays were 100% efficient (E=2, i.e., 2 copies are generated every cycle). As part of the optimization of the assays, the efficiencies of the assays have been determined to be >98%.

TABLE 5

CT values for carbapenem-resistant and ESBL-producing strains. KPC real-time PCR assays were performed in duplicate for all of the strains listed in Table 3. CT values were calculated using the ABI Sequence detection software following user defined background and CT. For a sample to be called, the CT value had to be within 6 StdDev of either control. All samples tested were within 6 StdDev of the known positive and negative controls. A total of 10 positive strains were identified out of the 24 tested.

| Strain ID | CT-KPC-87 | CT-KPC-289 | CT-KPC-758 | Avg CT | Call |
|---|---|---|---|---|---|
| 300960 | 30.02 | 28.72 | 29.67 | 29.5 | Negative |
|  | 30.33 | 28.04 | 29.97 |  |  |
| 300967 | 15.02 | 14.06 | 14.72 | 14.6 | Positive |
|  | 15.09 | 14 | 14.61 |  |  |
| 300996 | 18.56 | 17.37 | 18.16 | 18.1 | Positive |
|  | 18.66 | 17.44 | 18.33 |  |  |
| 301008 | 32.17 | 31.8 | 33.06 | 32.2 | Negative |
|  | 33.07 | 30.71 | 32.12 |  |  |
| 301888 | 17.59 | 16.52 | 17.44 | 17.3 | Positive |
|  | 17.71 | 17.02 | 17.61 |  |  |
| 301891 | 33.93 | 32.95 | 32.11 | 33.4 | Negative |
|  | 34.24 | 33.26 | 33.97 |  |  |
| 301892 | 17.73 | 16.74 | 17.49 | 17.4 | Positive |
|  | 17.87 | 17.02 | 17.55 |  |  |
| 301894 | 16.27 | 15.08 | 16.63 | 16.0 | Positive |
|  | 16.06 | 15.11 | 17.02 |  |  |
| 301896 | 31.98 | 30.48 | 30.99 | 31.3 | Negative |
|  | 32.17 | 31.25 | 30.97 |  |  |
| 301898 | 33.16 | 32.92 | 31.98 | 33.2 | Negative |
|  | 34.02 | 32.85 | 34.16 |  |  |
| 301899 | 32.1 | 31.06 | 32.33 | 31.6 | Negative |
|  | 31.57 | 30.96 | 31.35 |  |  |
| 301905 | 19.35 | 18.36 | 19.06 | 19.0 | Positive |
|  | 19.39 | 18.54 | 19.07 |  |  |
| 301916 | 16.64 | 15.66 | 16.82 | 16.4 | Positive |
|  | 16.57 | 15.55 | 16.93 |  |  |
| 301917 | 19.01 | 17.72 | 18.75 | 18.5 | Positive |
|  | 18.58 | 17.93 | 18.94 |  |  |
| 301918 | 16.25 | 15.24 | 17.18 | 16.2 | Positive |
|  | 16.18 | 15.32 | 17.14 |  |  |
| 301919 | 31.38 | 30.06 | 30.75 | 30.6 | Negative |
|  | 30.85 | 29.72 | 30.76 |  |  |
| 301920 | 31.59 | 31.22 | 31.71 | 31.6 | Negative |
|  | 31.65 | 31.19 | 32.19 |  |  |
| 301921 | 29.99 | 28.75 | 30.64 | 29.6 | Negative |
|  | 30.01 | 28.5 | 29.8 |  |  |
| 301922 | 31.9 | 30.88 | 31.83 | 31.4 | Negative |
|  | 32.29 | 30.74 | 30.94 |  |  |
| 303364 | 32.65 | 31.2 | 33.29 | 32.3 | Negative |
|  | 32.29 | 31.74 | 32.47 |  |  |
| 303365 | 31.96 | 31.15 | 31.47 | 31.4 | Negative |
|  | 32.53 | 30.02 | 31.48 |  |  |
| 303369 | 31.19 | 30.15 | 31.03 | 30.7 | Negative |
|  | 31.09 | 30.14 | 30.53 |  |  |
| 303375 | 28.12 | 27.03 | 27.99 | 27.7 | Negative |
|  | 27.9 | 27.35 | 28.01 |  |  |
| 303990 | 15.11 | 14.19 | 14.84 | 14.7 | Positive |
|  | 15.2 | 14.06 | 14.81 |  |  |

TABLE 6

Summary results from all strains and assays. Based on the call criteria established in Table 4, the average Intra-CT distance (max positive CT – min positive CT), the average CT and the average Inter-CT (positive Avg CT – negative Avg CT) distance for all positive and negative strains using the values from the KPC assays.

| Call-KPC Assays | Intra CT Distance* | Avg CT* | Inter CT Distance* |
|---|---|---|---|
| Positives | 4.4 | 16.8 | −14.4 CT |
| Negatives | 5.7 | 31.2 |  |

*These values were calculated using Average CT values found in Table 5. All replicate positive reactions within a given KPC assay were 0.3 StdDev of each other.

As noted earlier, there was not a reduction in sensitivity in the KPC-758 assay due to a one base pair mismatch in the reverse primer of the assay with the KPC-3 variant. This can be seen in Table 4 looking at the Avg CT for the sequence verified KPC-3 strain 301918 (Avg CT=16.2) compared to the KPC-1 strain 301916 (Avg CT=16.4) or the KPC-2 strain 301917 (Avg CT=18.5).

Sequencing real-time positive strains: To validate the real-time assays, all positive calls were sequence verified. Standard PCR was performed using primers (Yigit et al. 2001 (3) and Bratu et al. 2005 (5)) that amplify the entire open reading frame or coding sequence of the KPC gene. PCR amplicons were cleaned up and sequenced as described in the material and methods. The reverse strand of the PCR amplicon was sequenced and trimmed. Sequences were trimmed based on the quality values assessed by the KB basecaller in the Sequencing Analysis software v5.1 (Applied Biosystems, Foster City, Calif.). Bases with a quality value >20 were used for the NCBI comparison. The average length of read was >500 bp. The sequences were compared to the non-redundant sequences in GenBank using the BLAST algorithm from NCBI. All of the positives from the real-time assays matched the available GenBank KPC sequences with >99% coverage and >99% sequence identity and did not have any significant identity to any other gene. Therefore, these KPC real-time assays in this challenge set of strains performed with 100% sensitivity and 100% specificity, compared to the 58.8% sensitivity (7 False Negatives=Strain ID 300996, 301888, 301892, 301894, 301905, 301916, 301917) and 100% specificity performance of the CLSI standard microbroth dilution with a IPM resistance at ≧16 µg/ml (2).

Sensitivity Real Time PCR Assay: A 5 fold DNA dilution scheme (20 ng to 2 fg) was set up using a positive control strain (Strain ID 301916). The negative CT threshold was established for each assay using the negative controls (Strain ID 300960) within each the experiment. A 95% confidence interval (CI) was applied to the negative CT threshold. To calculate the CI, the historical standard deviation (StdDev) listed in Table 4 (0.9) was multiplied by 3 (0.9×3=2.7 or 3 CT), so that the CT threshold to call a sample negative was calculated to be 3 CTs minus the lowest negative control CT. The standard PCR reactions and primers (Forward #5 and Reverse #10) were used according to Yigit et al. 2001 and Woodford et al. 2004. Standard PCR reactions were run on gel electrophoresis and visualized using Ethiduim Bromide and a gel documentation system (Kodak 1D v3.6, New Haven, Conn.).

Direct Sample assay: A positive (Strain ID 301916) and negative (Strain ID 300960) strains were streaked out on TSA plates containing 5% Sheep red blood cells (BD Diagnostic Systems, Sparks, Md.) and grown at 35° C. overnight. Pure colonies of each strain were placed into Trypticase Soy Broth (TSB) (BD Diagnostic Systems, Sparks, Md.), quantified using a nephlometer (BD Diagnostic Systems, Sparks, Md.) and diluted to $1.0E^{+06}$, $1.0E^{+05}$, $1.0E^{+04}$ and $1.0E^{+03}$ CFU/ml in sterile urine. The bacteria were collected by centrifugation and the DNA was isolated using a standard heat lysis as described in the DNA extraction methodology. Five microliters of the supernatant containing the DNA was used in the Real-time PCR and standard PCR reactions. The standard PCR reactions and primers (numbering was taken from Yigit et al. Forward #5 and Reverse #10) were used according to Yigit et al. 2001 and Woodford et al. 2004. Pure positive and negative colonies were inoculated into Bactec aerobic bottles containing 5 ml of sterile blood and placed into a Bactec instrument (BD Diagnostic Systems, Sparks, Md.). When the instrument called the bottles positive, 100 μl aliquots were removed from the bottles and placed into 1.5 ml tubes. Bacteria were collected by centrifugation and the pellets were both directly heat lysed or washed twice with 100 μl of 85% saline and then heat lysed. Five microliters of the supernatant containing the DNA was used in the Real-time PCR and standard PCR reactions. Positive (Strain ID 301916) and negative (Strain ID 300960) template controls isolated from pure colonies were run in every assay to ensure PCR reactions were performing. The formula used to calculate genome copies or equivalents is as follows [number of copies=(amount (ng)*$6.022\times10^{23}$)/(length*$1\times10^{9}$*650)]. The estimated genome size or length of Strain ID 301919 *Klebsiella pneumoniae* is 2,900,000 bp.

Results

KPC Real-Time PCR Sensitivity assays: To determine the sensitivity of the Real-time assays described herein in comparison to known assays, a sensitivity assay comparison was set up. To set up these experiments, total nucleic acids were isolated from pure colonies from a KPC positive (Strain ID 301916) and negative (Strain ID 300960) strain using the heat lysis protocol outlined above in the material and methods. The nucleic acids were normalized to 100 ng/μl in TE buffer and then serially diluted (5 fold dilution scheme) to a range of 20 ng to 2 fg. A 5 μl aliquot of the nucleic acid sample was placed into Real-time PCR assays (KPC-87 and KPC-758) and a Standard (Std) PCR assay (primers from Yigit et al. 2001). All PCR assays were run in triplicate. The Real-time assays were run on the ABI 7500 Fast Real-time PCR System (Applied Biosystems, Foster City, Calif.) using a 2 stage 2 step PCR program for 40 cycles. Standard PCR reactions were run on ABI 2720 Thermal Cycler (Applied Biosystems, Foster City, Calif.) using the PCR program outlined in Yigit et al. 2001. Standard PCR reactions were run on gel electrophoresis and visualized using Ethiduim Bromide and a gel documentation system (Kodak 1D v3.6, New Haven, Conn.) (FIG. 1). Cycle threshold (CT) values for the Real-time PCR assays were calculated using the ABI Sequence Detection software v1.3.1 (Applied Biosystems, Foster City, Calif.) following user defined baseline and CT. CT was set in the exponential phase of the curves for the positive controls. The baseline for the analysis was set in a region ($3^{rd}$-$12^{th}$ cycle), which did not have any sample that crossed the CT. To determine a CT range for a negative call, the negative controls were analyzed within the experiment. The negative CT threshold was set based solely on negative controls run simultaneously in the experiment and not the historical negative CT threshold seen in Table 4. The reasoning behind this strategy is that the reagents (e.g. commercially available master mixes) used in these experiments have not been specifically optimized for these primer probe assays, and the performance of the negative control may vary based on these reagents. This negative control variance can have a significant effect on determining the sensitivity of these assays. To set up a 95% confidence interval (CI) for the negative control threshold, the historical standard deviation (StdDev) listed in Table 4 (0.9) was multiplied by 3 (0.9×3=2.7 or 3 CT), so that the CT threshold to call a sample negative was calculated to be 3 CTs minus the lowest negative control CT.

Using the lowest negative control CT value minus 3 CTs (CI) for each Real-time assay listed in Table 7, the negative CT threshold was calculated for each assay in this experiment. Based on this formula, the negative CT threshold for KPC-87 was >35 CT and KPC-758 was >30 CT. Therefore, the reliable sensitivity for both KPC-87 and KPC-758 assays was at a nucleic acid concentration of $1.3E^{-03}$ ng or 1.3 pg from a positive KPC strain. To translate this value into genome copies or equivalents, one has to assume the nucleic acid input is all genomic DNA and then use the equation found in the materials and methods section above. Using this formula we calculated that the Real-time assays can reliably detect 42 genome equivalents. In comparison to the real-time assays, the Std PCR assay had the ability to reliably detect a band within all of the three replicates at a nucleic acid concentration of $3.2E^{-02}$ ng or 32 pg from a positive KPC strain. We calculated that the Std PCR assay can reliably detect 1,000 genome equivalents. Therefore, the sensitivity of the Real-time assays described herein is at least 1 order of magnitude more sensitive than the Std PCR assay described in Yigit et al. 2001 and Woodford et al. 2004.

TABLE 7

Sensitivity experiments for KPC-87 and KPC-758. A DNA dilution scheme (20 ng to 2 fg) was set up using a positive control strain (301916). The negative CT threshold was established for each assay (>35 CT for KPC-87 and >30 for KPC-758) using the lowest negative control CT values (300960) minus 3 CT (CI). Based on these criteria, a reliable detection limit for KPC-87 is <31 CT and <29.5 CT for KPC-758. This places the sensitivity for both assays at 1.3 pg (42 genome equivalents).

| Strain ID | Dilution (ng) | Real Time Assay KPC-87 Ct | KPC-87 Avg Ct | KPC-758 Ct | KPC-758 Avg Ct |
|---|---|---|---|---|---|
| 301916 Positive | 2.0E+01 | 16.0 | 16.0 | 15.5 | 15.6 |
|  |  | 15.9 |  | 16.1 |  |
|  |  | 16.1 |  | 15.2 |  |
|  | 4.0E+00 | 17.8 | 18.0 | 16.8 | 17.1 |
|  |  | 17.6 |  | 17.3 |  |
|  |  | 18.6 |  | 17.2 |  |
|  | 8.0E−01 | 20.6 | 20.5 | 18.8 | 19.4 |
|  |  | 19.5 |  | 19.5 |  |
|  |  | 21.3 |  | 19.9 |  |
|  | 1.6E−01 | 23.3 | 23.0 | 21.4 | 21.9 |
|  |  | 22.1 |  | 22.1 |  |
|  |  | 23.8 |  | 22.4 |  |
|  | 3.2E−02 | 25.5 | 25.5 | 24.0 | 24.4 |
|  |  | 24.7 |  | 24.2 |  |
|  |  | 26.4 |  | 25.0 |  |
|  | 6.4E−03 | 28.0 | 28.2 | 25.8 | 26.4 |
|  |  | 27.2 |  | 26.3 |  |
|  |  | 29.2 |  | 27.2 |  |
|  | 1.3E−03 | 30.7 | 30.4 | 28.2 | 28.7 |
|  |  | 29.6 |  | 28.7 |  |
|  |  | 30.9 |  | 29.3 |  |
|  | 2.6E−04 | 32.3 | 32.4 | 30.7 | 31.0 |
|  |  | 31.9 |  | 30.9 |  |
|  |  | 33.0 |  | 31.5 |  |
|  | 5.1E−05 | 36.2 | 35.0 | 33.4 | 32.6 |
|  |  | 34.4 |  | 32.3 |  |
|  |  | 34.4 |  | 32.3 |  |
|  | 1.0E−05 | 37.7 | 35.8 | 35.1 | 33.7 |
|  |  | 35.6 |  | 33.1 |  |
|  |  | 34.0 |  | 32.9 |  |

TABLE 7-continued

Sensitivity experiments for KPC-87 and KPC-758. A DNA dilution scheme (20 ng to 2 fg) was set up using a positive control strain (301916). The negative CT threshold was established for each assay (>35 CT for KPC-87 and >30 for KPC-758) using the lowest negative control CT values (300960) minus 3 CT (CI). Based on these criteria, a reliable detection limit for KPC-87 is <31 CT and <29.5 CT for KPC-758. This places the sensitivity for both assays at 1.3 pg (42 genome equivalents).

| | | Real Time Assay | | | |
|---|---|---|---|---|---|
| Strain | Dilution | KPC-87 | | KPC-758 | |
| ID | (ng) | Ct | Avg Ct | Ct | Avg Ct |
| | 2.0E−06 | 37.8 | 36.3 | >40 | 33.5 |
| | | 37.0 | | 33.8 | |
| | | 34.0 | | 33.2 | |
| 300960 | 2.00E+01 | ND | ND | ND | ND |
| Negative | | ND | | 35.37 | |
| | | 38.7 | | 33.09 | |

ND (not detected) the fluorescent signal did not cross the CT within the 40 cycles.

Direct Sample analysis: To determine the ability of the Real-time assays (KPC-87 and KPC-758) to detect KPC in primary or direct samples (blood and urine) and to compare this ability to the Std PCR assay, a direct sample comparison assay was performed. To set up the urine direct sample experiments, pure colonies of each strain (301916 and 300960) were placed into Trypticase Soy Broth (TSB) (BD Diagnostic Systems, Sparks, Md.), quantified using a nephlometer (BD Diagnostic Systems, Sparks, Md.), and subsequently diluted to $1.0E^{+06}$, $1.0E^{+05}$, $1.0E^{+04}$ and $1.0E^{+03}$ CFU/ml in sterile urine. The bacteria were collected by centrifugation and the DNA was isolated using a standard heat lysis as described in the DNA extraction methodology. A 5 μl aliquot of the nucleic acid sample was placed into Real-time PCR assays (KPC-87 and KPC-758) and a Standard (Std) PCR assay (primers from Yigit et al. 2001). All PCR assays were run in triplicate. The Real-time assays and Standard PCR reactions were run and analyzed as described previously. Based on the negative control CT values listed in Table 8, the negative CT threshold was established for each assay using the lowest negative CT values for each assay minus 3 CT (CI). Based on these criteria, the negative CT threshold for both KPC-87 and KPC-758 is >35 CT. For this experiment, the lowest CT on the KPC-758 assay was used as a conservative value for the negative control due to the fact that KPC-87 did not have a CT. Therefore, a reliable positive CT call or detection limit for KPC-87 was <33 and <32 CT for KPC-758, which translates into a reliable detection level of $1.0E^{+04}$ CFU/ml in a urine sample. This level is very important due to the fact that the average bioburden associated with a urinary tract infection (UTI) is $1.0E^{+05}$ CFU/ml. With further optimization it may be possible to drive the sensitivity even lower. The same nucleic acids extracted from these urine samples were also analyzed using the Std PCR primers. None of the samples produced a band with the exception of the positive template control (PTC). Therefore, the Std PCR assay described in both Yigit et al. 2001 and Woodford et al. 2004 cannot function in direct urine samples. Positive (Strain ID 301916) and negative (Strain ID 300960) template controls isolated from pure colonies were run in every assay to ensure PCR reactions were performing.

To set up the blood direct sample experiments, pure colonies of each strain (Strain 301916 and Strain 300960) were inoculated into Bactec aerobic plus bottles containing 5 ml of sterile blood and placed into a Bactec instrument (BD Diagnostic Systems, Sparks, Md.). When the instrument called the bottles positive, 100 μl aliquots were removed from the bottles and placed into 1.5 ml tubes. The bacteria were collected by centrifugation and the pellets were either directly heat lysed or washed and then heat lysed. A 5 μl aliquot of the nucleic acid sample was placed into the Real-time PCR assays (KPC-87 and KPC-758) and the Std PCR assay (Yigit et al. 2001). All PCR assays were run in triplicate. The Real-time assays and Standard PCR reactions were run and analyzed as described previously. The calculated negative CT threshold for both KPC-87 and KPC-758 was >33 CT. Therefore, a reliable positive CT call or detection limit for KPC-87 was <30 and <28 CT for KPC-758. Using the standard curve information in Table 7, the detection level for both of these assays in blood was approximately 6.4 pg or 2,000 genomic equivalents. When considering that the blood was diluted from the positive Bactec bottle 1/100 (100 μl sample (1/10) and analyzed 5 μl of 50 μl total (1/10)), then the initial CFU/ml in the positive Bactec bottle was $2.0E^{+05}$ CFU/ml. This result is very important due to the theory that the average CFU/ml for a positive Bactec bottle containing *Klebsiella* spp. would be between $1.0E^{+05}$ to $1.0E^{+06}$ CFU/ml.

Figure 2:
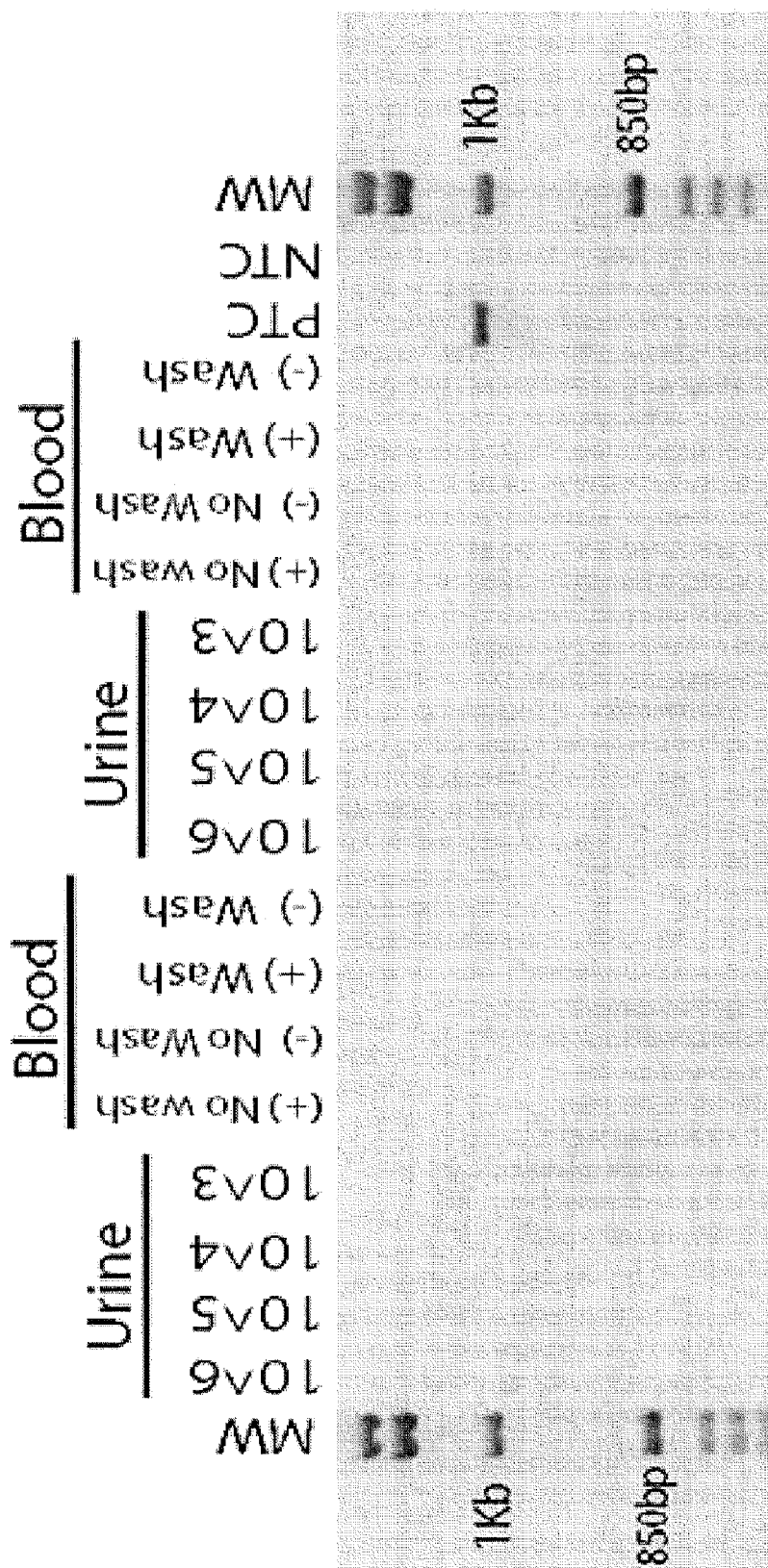
FIG. 2: Direct sample experiments for Standard PCR. The DNA extracted from the urine and blood samples was also used to inoculate the standard PCR reactions. Not pictured in this gel are the urine negative control samples which were run on a separate gel and did not contain any bands. None of the samples produced bands with the except the positive template control (PTC).

As seen in FIG. 2, the Std PCR primers did not produce a visible band with the exception of the positive template control (PTC). Therefore, the Std PCR assay described in both Yigit et al. 2001 and Woodford et al. 2004 cannot function in positive blood culture samples. Positive (Strain ID 301916) and negative (Strain ID 300960) template controls isolated from pure colonies were run in every assay to ensure PCR reactions were performing.

TABLE 8

Direct sample experiments for KPC-87 and KPC-758. Positive (301916) and negative controls (300960) were spiked into either sterile blood or urine samples as described in the methods. A urine negative CT threshold >35CT was established for both Real-time assays. Based on these criteria, a reliable positive CT call for KPC-87 is <33 CT and <32 CT for KPC-758, which translates into a reliable detection level of $1.0E^{+04}$ CFU/ml in a urine sample. A blood negative CT threshold >33CT was established for both Real-time assays and a reliable positive CT call or detection limit for KPC-87 was <30 and <28 CT for KPC-758. Using the standard curve CT information from Table 7 the detection level for both of these assays in blood is approximately 6.4 pg or 2,000 genomic equivalents.

| | | | KPC-87 | | KPC-758 | |
|---|---|---|---|---|---|---|
| Strain ID | Sample | CFU | Ct | Mean Ct | Ct | Mean Ct |
| 301916 Positive | Urine | 1.00E+06 | 23.8 | 23.8 | 22.3 | 22.2 |
| | | | 23.8 | | 22.1 | |
| | | 1.00E+05 | 28.3 | 27.8 | 25.3 | 25.6 |
| | | | 27.2 | | 25.8 | |
| | | 1.00E+04 | 32.6 | 31.9 | 31.0 | 30.1 |
| | | | 31.2 | | 29.1 | |
| | | 1.00E+03 | 37.0 | 35.6 | 34.4 | 33.4 |
| | | | 34.2 | | 32.5 | |
| 300960 Negative | Urine | 1.00E+06 | ND | | ND | |
| | | | ND | | 38.3 | |
| 301916 Positive | Blood, unwashed | NA | 29.6 | 28.2 | 27.3 | 25.8 |
| | | | 26.9 | | 24.2 | |
| | Blood, washed | NA | 31.1 | 31.3 | 28.3 | 29.1 |
| | | | 31.4 | | 30.0 | |
| 300960 Negative | Blood, unwashed | NA | 37.2 | 36.8 | 38.5 | 37.6 |
| | | | 36.4 | | 36.7 | |
| | Blood, washed | NA | 37.2 | 36.7 | 36.6 | 36.0 |
| | | | 36.3 | | 35.4 | |
| PTC | PTC | | 17.1 | | 16.4 | |
| NTC | NTC | | 35.1 | | ND | |

NA (not available) the CFU (Colony Forming Units) values were not calculated,
ND (not detected) the fluorescent signal did not cross the CT within the 40 cycles.

References
1. Clinical and Laboratory Standard Institute. 2006. Methods for Dilution Antimicrobial Susceptibility Tests for Bacteria That Grow Aerobically; Approved Standard-Seventh Edition M7-A7. Clinical and Laboratory Standard Institute, Wayne, Pa.
2. Clinical and Laboratory Standard Institute. 2007. Performance Standards for Antimicrobial Susceptibility Testing; Seventeenth Informational Supplement M100-S17. Clinical and Laboratory Standard Institute, Wayne, Pa.
3. Yigit et al. 2001. Novel carbapenem-hydrolyzing β-lactamase, KPC-1, from a carbapenem-resistant strain of *Klebsiella pneumoniae*. *Antimicrob. Agents Chemother* 45:1151-1161.
4. Moland et al. 2003. Plasmid-mediated, carbapenem-hydrolysing b-lactamase, KPC-2, in *Klebsiella pneumoniae* isolates. *Journal of Antimicrobial Chemotherapy* 51:711-714.
5. Bratu et al. 2005. Carbapenemase-producing *Klebsiella pneumoniae* in Brooklyn, N.Y.: molecular epidemiology and in vitro activity of polymyxin B and other agents. *Journal of Antimicrobial Chemotherapy* 56:128-132.
6. Bratu et al. 2005a. Rapid spread of carbapenem-resistant *Klebsiella pneumoniae* in New York City: a new threat to our antibiotic armamentarium. *Arch Intern Med.* 165(12):1430-5.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule for identifying a bacteria containing carbapenemase said nucleic acid molecule selected from the group consisting of SEQ ID NOS:15-20.

2. The nucleic acid molecule of claim 1, which is unlabeled.

3. The nucleic acid molecule of claim 2, selected from the group consisting of SEQ ID NOs:15, 17, 19, and 20.

4. The nucleic acid molecule of claim 1, wherein said molecule is labeled and is useful as a probe.

5. The nucleic acid molecule of claim 4, which is SEQ ID NO:18.

* * * * *